United States Patent
Garfield et al.

(10) Patent No.: US 10,238,576 B2
(45) Date of Patent: *Mar. 26, 2019

(54) CLOSED FLUID TRANSFER SYSTEM

(71) Applicant: J & J SOLUTIONS, INC., Coralville, IA (US)

(72) Inventors: Jared Michael Garfield, North Liberty, NY (US); Randall Scott Koplin, Sun Prairie, NY (US); Kent Jeffrey Kallsen, Jefferson, WI (US); Daniel Juhyung Lee, Monticello, WI (US); Stephen R. Mitchell, Green Oaks, IL (US); John R. Slump, Iowa City, IA (US)

(73) Assignee: J & J SOLUTIONS, INC., Coralville, IA (US)

( * ) Notice: Subject to any disclaimer, the term of this patent is extended or adjusted under 35 U.S.C. 154(b) by 287 days.

This patent is subject to a terminal disclaimer.

(21) Appl. No.: 15/150,855

(22) Filed: May 10, 2016

(65) Prior Publication Data

US 2016/0250102 A1 Sep. 1, 2016

Related U.S. Application Data

(60) Continuation of application No. 14/681,178, filed on Apr. 8, 2015, now Pat. No. 9,370,466, which is a
(Continued)

(51) Int. Cl.
*A61J 1/20* (2006.01)
*A61J 1/10* (2006.01)
(Continued)

(52) U.S. Cl.
CPC ............... *A61J 1/201* (2015.05); *A61J 1/10* (2013.01); *A61J 1/20* (2013.01); *A61J 1/2051* (2015.05);
(Continued)

(58) Field of Classification Search
CPC .. A61J 1/20; A61J 1/201; A61J 1/2048; A61J 1/2051
See application file for complete search history.

(56) References Cited

U.S. PATENT DOCUMENTS 3,706,305 A   12/1972   Berger et al.
4,180,070 A   12/1979   Genese
(Continued)

FOREIGN PATENT DOCUMENTS

DE   60222059 T2   12/2007
EP   0521264 A2   1/1993
(Continued)

OTHER PUBLICATIONS

Extended European Search Report corresponding to EP 11 78 7309.1 dated Aug. 3, 2015; 9 pp.
(Continued)

*Primary Examiner* — Susan S Su
(74) *Attorney, Agent, or Firm* — Carter, Deluca & Farrell LLP

(57) ABSTRACT

A closed fluid transfer system for fluidly interconnecting a syringe to any one of a patient I.V. set, a vial and an I.V. bag, is provided and includes a first adapter defining a lumen and supporting a seal across a first end of its lumen, the first adapter supporting a rear end of a needle within the lumen, wherein the seal is movable relative to the needle such that a tip of the needle penetrates through the seal; and a second adapter defining a lumen and supporting a seal across a first end of its lumen; wherein when the second adapter is coupled to the first adapter, the second adapter seal abuts the first adapter seal and moves the first adapter seal relative to the tip of the needle such that the tip of the needle penetrates through the abutting first adapter seal and second adapter seal.

8 Claims, 27 Drawing Sheets

Related U.S. Application Data division of application No. 13/699,908, filed as application No. PCT/US2011/037873 on May 25, 2011, now Pat. No. 9,107,809.

(60) Provisional application No. 61/348,820, filed on May 27, 2010, provisional application No. 61/348,832, filed on May 27, 2010, provisional application No. 61/419,029, filed on Dec. 2, 2010, provisional application No. 61/419,039, filed on Dec. 2, 2010.

(51) Int. Cl.
*A61M 5/162* (2006.01)
*A61M 39/10* (2006.01)

(52) U.S. Cl.
CPC ........... *A61J 1/2055* (2015.05); *A61J 1/2065* (2015.05); *A61J 1/2072* (2015.05); *A61J 1/2075* (2015.05); *A61J 1/2096* (2013.01); *A61M 5/162* (2013.01); *A61M 39/1011* (2013.01); *A61J 1/2089* (2013.01); *A61M 2039/1027* (2013.01); *A61M 2039/1072* (2013.01); *A61M 2039/1077* (2013.01)

(56) References Cited

U.S. PATENT DOCUMENTS

| | | | |
|---|---|---|---|
| 4,201,208 | A | 5/1980 | Cambio, Jr. |
| 4,576,211 | A | 3/1986 | Valentini et al. |
| 4,673,404 | A | 6/1987 | Gustavsson |
| 4,752,292 | A | 6/1988 | Lopez et al. |
| 4,872,494 | A * | 10/1989 | Coccia .................. A61J 1/2096 141/27 |
| 5,100,394 | A | 3/1992 | Dudar et al. |
| 5,135,489 | A | 8/1992 | Jepson et al. |
| 5,158,554 | A | 10/1992 | Jepson et al. |
| 5,167,648 | A | 12/1992 | Jepson et al. |
| 5,188,620 | A | 2/1993 | Jepson et al. |
| 5,211,638 | A | 5/1993 | Dudar et al. |
| 5,405,340 | A | 4/1995 | Fageol et al. |
| 5,437,650 | A | 8/1995 | Larkin et al. |
| 5,470,327 | A | 11/1995 | Helgren et al. |
| 5,507,733 | A | 4/1996 | Larkin et al. |
| 5,520,666 | A | 5/1996 | Choudhury et al. |
| 5,545,152 | A | 8/1996 | Funderburk et al. |
| 5,549,566 | A | 8/1996 | Elias et al. |
| 5,580,351 | A | 12/1996 | Helgren et al. |
| 5,658,260 | A | 8/1997 | Desecki et al. |
| 5,685,842 | A | 11/1997 | Drivas |
| 5,702,374 | A | 12/1997 | Johnson |
| 5,785,682 | A | 7/1998 | Grabenkort |
| 5,785,692 | A | 7/1998 | Attermeier et al. |
| 5,797,897 | A | 8/1998 | Jepson et al. |
| 5,807,345 | A | 9/1998 | Grabenkort |
| 5,810,768 | A | 9/1998 | Lopez |
| 5,871,500 | A | 2/1999 | Jepson et al. |
| 5,891,129 | A | 4/1999 | Daubert et al. |
| 5,899,888 | A | 5/1999 | Jepson et al. |
| 5,924,584 | A | 7/1999 | Hellstrom et al. |
| 5,954,104 | A | 9/1999 | Daubert et al. |
| 5,954,708 | A | 9/1999 | Lopez et al. |
| 5,957,898 | A | 9/1999 | Jepson et al. |
| 5,964,785 | A | 10/1999 | Desecki et al. |
| 6,063,068 | A | 5/2000 | Fowles et al. |
| 6,083,194 | A | 7/2000 | Lopez |
| 6,090,091 | A | 7/2000 | Fowles et al. |
| 6,139,534 | A | 10/2000 | Niedospial, Jr. et al. |
| 6,193,697 | B1 | 2/2001 | Jepson et al. |
| 6,213,996 | B1 | 4/2001 | Jepson et al. |
| 6,245,048 | B1 | 6/2001 | Fangrow, Jr. et al. |
| 6,261,266 | B1 | 7/2001 | Jepson et al. |
| 6,261,282 | B1 | 7/2001 | Jepson et al. |
| 6,302,289 | B1 | 10/2001 | Andersson et al. |
| 6,344,033 | B1 | 2/2002 | Jepson et al. |
| 6,387,074 | B1 | 5/2002 | Horppu et al. |
| 6,394,983 | B1 | 5/2002 | Mayoral et al. |
| 6,409,708 | B1 | 6/2002 | Wessman |
| 6,428,520 | B1 | 8/2002 | Lopez et al. |
| 6,447,498 | B1 | 9/2002 | Jepson et al. |
| 6,524,295 | B2 | 2/2003 | Daubert et al. |
| 6,569,125 | B2 | 5/2003 | Jepson et al. |
| 6,595,964 | B2 | 7/2003 | Finley et al. |
| 6,599,273 | B1 | 7/2003 | Lopez |
| 6,605,576 | B2 | 8/2003 | Lee |
| 6,635,043 | B2 | 10/2003 | Daubert et al. |
| 6,635,044 | B2 | 10/2003 | Lopez |
| 6,660,527 | B2 | 12/2003 | Stroup |
| 6,669,681 | B2 | 12/2003 | Jepson et al. |
| 6,695,817 | B1 | 2/2004 | Fangrow, Jr. |
| D488,867 | S | 4/2004 | Chau |
| 6,715,520 | B2 | 4/2004 | Andreasson et al. |
| 6,871,838 | B2 | 3/2005 | Raines et al. |
| 6,874,522 | B2 | 4/2005 | Anderson et al. |
| 6,875,205 | B2 | 4/2005 | Leinsing |
| 7,025,389 | B2 | 4/2006 | Cuschieri et al. |
| 7,040,598 | B2 | 5/2006 | Raybuck |
| 7,044,441 | B2 | 5/2006 | Doyle |
| 7,100,891 | B2 | 9/2006 | Doyle |
| 7,114,701 | B2 | 10/2006 | Peppel |
| 7,175,615 | B2 | 2/2007 | Hanly et al. |
| 7,244,249 | B2 | 7/2007 | Leinsing et al. |
| 7,306,198 | B2 | 12/2007 | Doyle |
| 7,306,584 | B2 | 12/2007 | Wessman et al. |
| 7,314,061 | B2 | 1/2008 | Peppel |
| 7,316,669 | B2 | 1/2008 | Ranalletta |
| 7,358,505 | B2 | 4/2008 | Woodworth et al. |
| 7,396,051 | B2 | 7/2008 | Baldwin et al. |
| 7,425,209 | B2 | 9/2008 | Fowles et al. |
| 7,470,258 | B2 | 12/2008 | Barker et al. |
| 7,497,848 | B2 | 3/2009 | Leinsing et al. |
| 7,497,849 | B2 | 3/2009 | Fangrow, Jr. |
| 7,503,908 | B2 | 3/2009 | Bartholomew |
| 7,510,545 | B2 | 3/2009 | Peppel |
| 7,563,253 | B2 | 7/2009 | Tanner et al. |
| 7,569,036 | B2 | 8/2009 | Domkowski et al. |
| 7,569,043 | B2 | 8/2009 | Fangrow |
| 7,591,449 | B2 | 9/2009 | Raines et al. |
| 7,615,035 | B2 | 11/2009 | Peppel |
| 7,645,271 | B2 | 1/2010 | Fangrow |
| 7,645,274 | B2 | 1/2010 | Whitley |
| 7,648,491 | B2 | 1/2010 | Rogers |
| 7,651,481 | B2 | 1/2010 | Raybuck |
| 7,670,326 | B2 | 3/2010 | Shemesh |
| 7,713,247 | B2 | 5/2010 | Lopez |
| 7,717,883 | B2 | 5/2010 | Lopez |
| 7,717,884 | B2 | 5/2010 | Lopez |
| 7,717,886 | B2 | 5/2010 | Lopez |
| 7,743,799 | B2 | 6/2010 | Mosler et al. |
| 7,744,581 | B2 | 6/2010 | Wallen et al. |
| 7,753,338 | B2 | 7/2010 | Desecki |
| 7,758,560 | B2 | 7/2010 | Connell et al. |
| 7,762,524 | B2 | 7/2010 | Cawthon et al. |
| 7,763,013 | B2 | 7/2010 | Baldwin et al. |
| 7,763,199 | B2 | 7/2010 | Fangrow, Jr. |
| 7,766,304 | B2 | 8/2010 | Phillips |
| 7,766,897 | B2 | 8/2010 | Ramsey et al. |
| 7,900,659 | B2 | 3/2011 | Whitley et al. |
| 8,043,864 | B2 | 10/2011 | Stroup |
| 8,119,419 | B2 | 2/2012 | Stroup |
| 8,122,923 | B2 | 2/2012 | Kraus et al. |
| 8,157,784 | B2 | 4/2012 | Rogers |
| 8,251,346 | B2 | 8/2012 | Stroup |
| 8,287,513 | B2 | 10/2012 | Ellstrom et al. |
| 8,414,554 | B2 | 4/2013 | Garfield et al. |
| 8,414,555 | B2 | 4/2013 | Garfield et al. |
| 8,414,556 | B2 | 4/2013 | Garfield et al. |
| 8,469,940 | B2 | 6/2013 | Garfield et al. |
| 8,894,627 | B2 | 11/2014 | Garfield et al. |
| 9,039,047 | B2 | 5/2015 | Imai |
| 9,370,466 | B2 | 6/2016 | Garfield et al. |
| 9,933,094 | B2 * | 4/2018 | Fangrow ............... A61M 39/26 |
| 2002/0115981 | A1 | 8/2002 | Wessman |
| 2002/0177819 | A1 | 11/2002 | Barker et al. |

(56) References Cited

U.S. PATENT DOCUMENTS

| | | |
|---|---|---|
| 2003/0070726 A1 | 4/2003 | Andreasson et al. |
| 2003/0187420 A1 | 10/2003 | Akerlund et al. |
| 2004/0124389 A1 | 7/2004 | Phillips |
| 2004/0144668 A1 | 7/2004 | Marshall et al. |
| 2006/0106360 A1 | 5/2006 | Wong |
| 2006/0129109 A1 | 6/2006 | Shaw et al. |
| 2006/0276770 A1* | 12/2006 | Rogers ............... A61J 1/2089 604/414 |
| 2007/0015233 A1 | 1/2007 | Brancia |
| 2007/0079894 A1 | 4/2007 | Kraus et al. |
| 2007/0088315 A1 | 4/2007 | Haindl |
| 2007/0101772 A1 | 5/2007 | Duncan et al. |
| 2008/0097371 A1 | 4/2008 | Shemesh |
| 2008/0103455 A1 | 5/2008 | Domkowski et al. |
| 2008/0103485 A1 | 5/2008 | Kruger |
| 2008/0142388 A1 | 6/2008 | Whitley et al. |
| 2008/0172024 A1 | 7/2008 | Yow |
| 2008/0223484 A1 | 9/2008 | Horppu |
| 2008/0249498 A1 | 10/2008 | Fangrow |
| 2008/0262465 A1 | 10/2008 | Zinger et al. |
| 2008/0264450 A1 | 10/2008 | Baldwin et al. |
| 2008/0287920 A1 | 11/2008 | Fangrow et al. |
| 2008/0318456 A1 | 12/2008 | Yow et al. |
| 2009/0069783 A1 | 3/2009 | Ellstrom et al. |
| 2009/0216212 A1 | 8/2009 | Fangrow, Jr. |
| 2009/0243281 A1 | 10/2009 | Seifert et al. |
| 2009/0270832 A1 | 10/2009 | Vancaillie et al. |
| 2009/0326506 A1 | 12/2009 | Hasegawa et al. |
| 2010/0004602 A1 | 1/2010 | Nord et al. |
| 2010/0004618 A1 | 1/2010 | Rondeau et al. |
| 2010/0004619 A1 | 1/2010 | Rondeau et al. |
| 2010/0004634 A1 | 1/2010 | Whitley |
| 2010/0036330 A1 | 2/2010 | Plishka et al. |
| 2010/0049160 A1 | 2/2010 | Jepson et al. |
| 2010/0055668 A1 | 3/2010 | Stroup |
| 2010/0106129 A1 | 4/2010 | Goeckner et al. |
| 2010/0108681 A1 | 5/2010 | Jepson et al. |
| 2010/0147402 A1 | 6/2010 | Tornqvist |
| 2010/0152669 A1 | 6/2010 | Rosenquist |
| 2010/0160889 A1 | 6/2010 | Smith et al. |
| 2010/0217226 A1 | 8/2010 | Shemesh |
| 2010/0218846 A1 | 9/2010 | Kriheli |
| 2010/0241088 A1 | 9/2010 | Ranalletta et al. |
| 2010/0249745 A1 | 9/2010 | Ellstrom |
| 2011/0015580 A1 | 1/2011 | Stroup |
| 2011/0049866 A1 | 3/2011 | Trombley, III et al. |
| 2011/0106046 A1* | 5/2011 | Hiranuma ............ A61J 1/2096 604/414 |
| 2011/0266477 A1 | 11/2011 | Stroup |
| 2012/0157914 A1 | 6/2012 | Stroup |
| 2012/0179128 A1* | 7/2012 | Takemoto ............ A61M 5/162 604/414 |
| 2015/0068640 A1 | 3/2015 | Garfield et al. |

FOREIGN PATENT DOCUMENTS

| | | |
|---|---|---|
| EP | 0667126 A1 | 8/1995 |
| EP | 1279798 A2 | 1/2003 |
| EP | 2144589 A1 | 1/2010 |
| JP | 08182742 | 7/1996 |
| JP | 2002126094 A | 5/2002 |
| JP | 2005522281 A | 7/2005 |
| JP | 2007509691 A | 4/2007 |
| WO | 9320767 A1 | 10/1993 |
| WO | 9320768 A1 | 10/1993 |
| WO | 9634571 A1 | 11/1996 |
| WO | 9748449 A1 | 12/1997 |
| WO | 9748450 A1 | 12/1997 |
| WO | 9748451 A1 | 12/1997 |
| WO | 9956642 A1 | 11/1999 |
| WO | 9956643 A1 | 11/1999 |
| WO | 9956812 A2 | 11/1999 |
| WO | 0049957 A1 | 8/2000 |
| WO | 0057811 A1 | 10/2000 |
| WO | 01060235 A2 | 8/2001 |
| WO | 0278777 A1 | 10/2002 |
| WO | 03034932 A1 | 5/2003 |
| WO | 03039385 A2 | 5/2003 |
| WO | 03047043 A1 | 6/2003 |
| WO | 0388858 A1 | 10/2003 |
| WO | 03088806 A2 | 10/2003 |
| WO | 2005002492 A1 | 1/2005 |
| WO | 2005011049 A2 | 2/2005 |
| WO | 2005041846 A2 | 5/2005 |
| WO | 2006052655 A2 | 5/2006 |
| WO | 2007101772 A1 | 9/2007 |
| WO | 2008136720 A1 | 11/2008 |
| WO | 2009035384 A1 | 3/2009 |
| WO | 2009133754 A1 | 11/2009 |
| WO | 2009140511 A1 | 11/2009 |
| WO | 2011150037 A1 | 12/2011 |

OTHER PUBLICATIONS

I Chou, C.K. (1995). "Radiofrequency Hyperthermia in Cancer Therapy," Biologic Effects of Nonionizing Electromagnetic Fields. Chapter 94, CRC Press, Inc. pp. 1424-1428.

Urologix, Inc.—Medical Professionals: Targis3 Technology (a date prior to the filing of the present application) <http://www.urologix.com/medical/technology.html (3> total pages).

International Search Report corresponding to European Application No. EP 06 00 9435.6; completed Jul. 6, 2006 and dated Jul. 13, 2006; 3 pp.

International Search Report corresponding to International Application No. PCT/US2009/043976, completed Jun. 26, 2009 and dated Jul. 28, 2009; 3 pp.

International Search Report and Written Opinion corresponding to PCT/US2011/037873, completed Sep. 6, 2011 and dated Sep. 13, 2011; 34 pp.

New Zealand First Examination Report corresponding to NZ 603808 dated Jul. 11, 2013; 2 pp.

Australian Examination Report No. 1 corresponding to AU 2011258371 dated Dec. 19, 2013; 3 pp.

Canadian Office Action corresponding to CA 2,800,278 dated Jul. 15, 2014; 2 pp.

New Zealand First Examination Report corresponding to NZ 627328 dated Jul. 24, 2014; 2 pp.

New Zealand Further Examination Report corresponding to NZ 603808 dated Sep. 3, 2014; 2 pp.

New Zealand First Examination Report corresponding to NZ 629637 dated Sep. 3, 2014; 2 pp.

New Zealand Further Examination Report corresponding to NZ 627328 dated Feb. 23, 2015; 2 pp.

Japanese Office Action corresponding to JP 2013-512192, dated Mar. 24, 2015 with the English Translation; 8 pp.

Extended European Search Report corresponding to EP 15 17 3144.5 dated Oct. 19, 2015.

Australian Examination Report No. 1 corresponding to AU 2014277764 dated Nov. 13, 2015.

Extended European Search Report corresponding to EP 15 17 6012.1 dated Nov. 13, 2015.

Extended European Search Report corresponding to EP 15 17 6026.1 dated Nov. 13, 2015.

Extended European Search Report corresponding to EP 15 17 6031.1 dated Nov. 19, 2015.

Extended European Search Report corresponding to EP 15 17 6044.4 dated Nov. 23, 2015.

\* cited by examiner

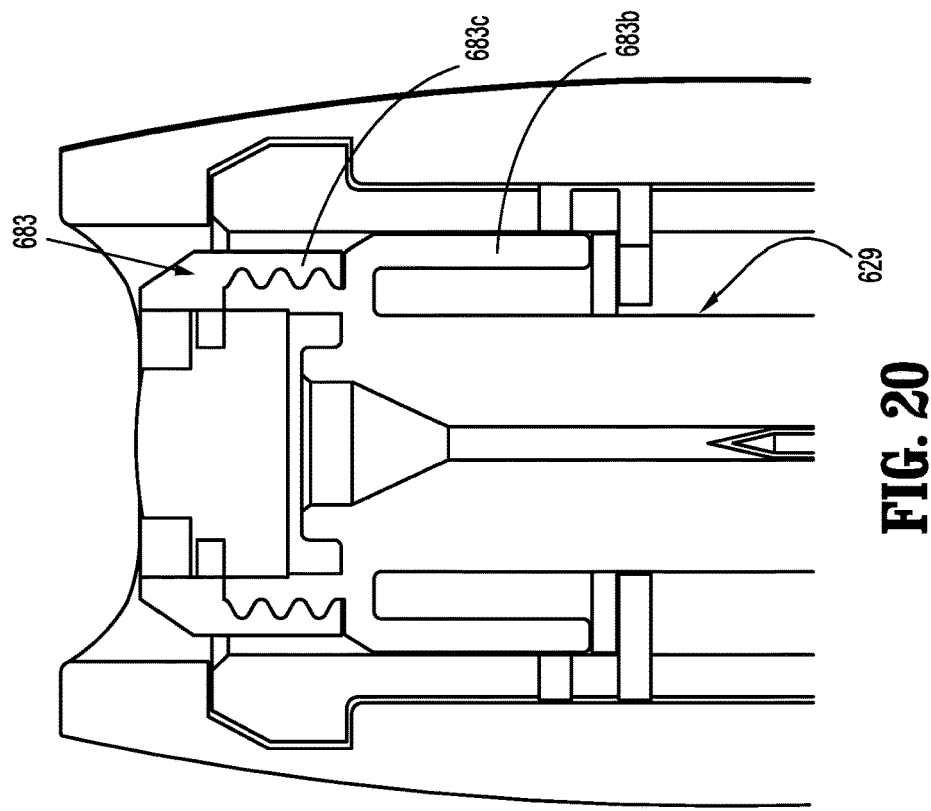
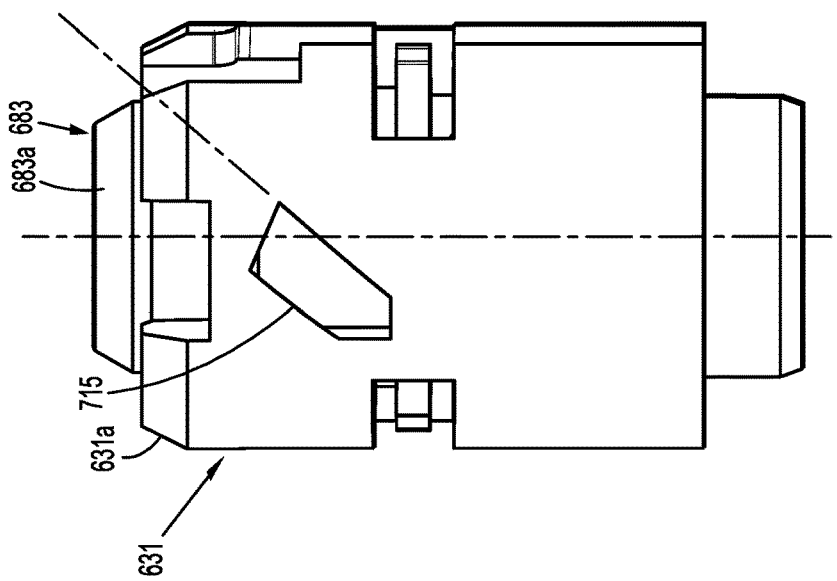

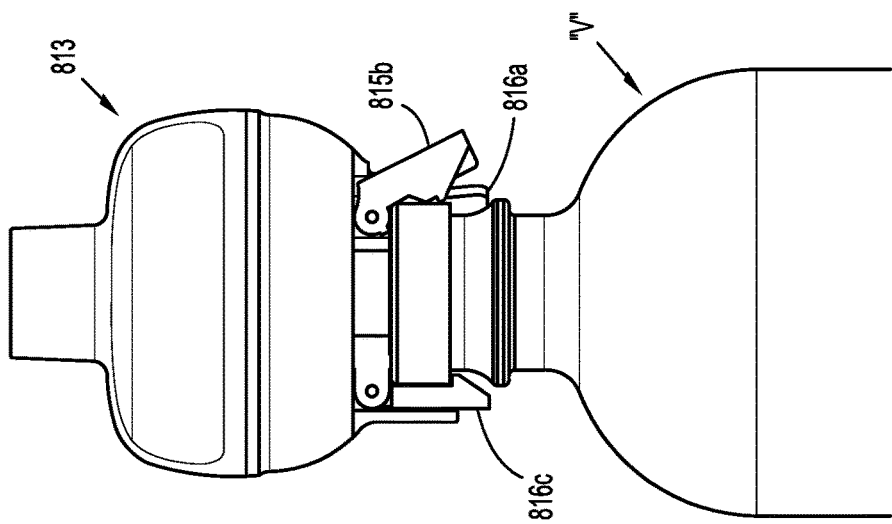
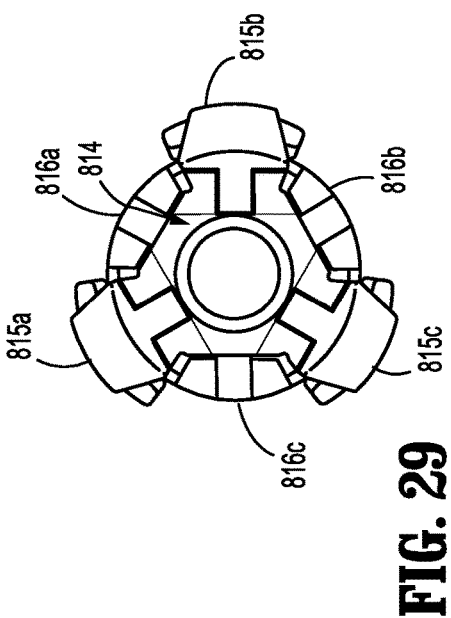
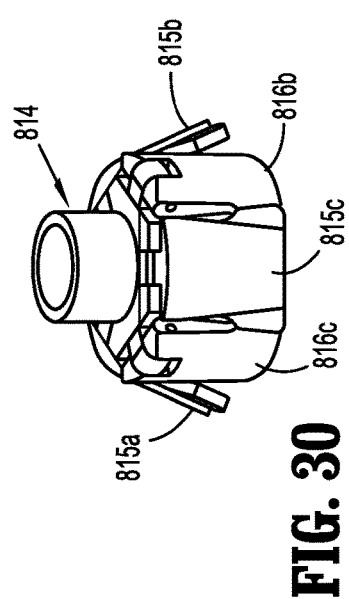

CLOSED FLUID TRANSFER SYSTEM

CROSS-REFERENCE TO RELATED APPLICATIONS

The present application is a Continuation Application which claims the benefit of and priority to U.S. patent application Ser. No. 14/681,178, filed on Apr. 8, 2015, which is a Divisional Application which claims the benefit of and priority to U.S. patent application Ser. No. 13/699,908, filed on Nov. 26, 2012 (now U.S. Pat. No. 9,107,809), which claims the benefit of and priority to International Patent Application Serial No. PCT/US11/037873, filed on May 25, 2011, which claims the benefit of and priority to each of U.S. Provisional Application Ser. No. 61/348,820, filed on May 27, 2010; U.S. Provisional Application Ser. No. 61/348,832, filed on May 27, 2010; U.S. Provisional Application Ser. No. 61/419,029, filed on Dec. 2, 2010; and U.S. Provisional Application Ser. No. 61/419,039, filed on Dec. 2, 2010; the entire content of each of which being incorporated herein by reference.

BACKGROUND

1. Technical Field

The present disclosure relates generally to closed fluid transfer systems and their related components, and more particularly, to components and systems for the transfer of gases/liquids/fluid or other substances from a first container to a second container while maintaining a closed system.

2. Background of Related Art

In one instance, hazardous medicines are frequently applied in the treatment of certain diseases, in particular, for example, in the treatment of cancer. Cytotoxic drugs have generally been used to kill cancer cells. However, the use of cytotoxic drugs, in the treatment of cancer cells, presents specific dangers to all cells, both in the patient and in healthcare providers. Although the exposure to a health care provider is normally very small for each cytotoxic drug dose administration, evidence suggests that chronic, low-dose exposure can produce significant health problems. Accordingly, a system that allows the safe handling of hazardous drugs while significantly reducing and/or eliminating the exposure to providers would be of great benefit.

Drugs are typically supplied in glass or plastic vials that are capped with a gas impermeable liquid seal or stopper. In some instances, the vial contents are a solid powder, such that a liquid needs to be injected for mixing (e.g., reconstitution). The injection of additional contents (e.g., liquid) into the vial produces an increased pressure which stresses the seal or stopper. Although the vial is intended to be sealed to liquid and gases, drug molecules in vapor phase can leak or pass around the sides of the stopper or through the stopper as the injection needle is withdrawn, thus presenting a hazard to the provider or clinician.

Accordingly, with the potential for aerosol leakage, leakage/spraying upon needle withdrawal, or spills, a means with which to prevent the accidental vapor phase drug egress is required.

Thus, the need exists for new components and systems capable of transferring gases/fluids/liquids or other substances between a conventional syringe and one of a vial, a patient I.V. (intra-venous) set, or an I.V. bag without leaking or spilling and without exposure of the liquids to substances outside the closed system. As such, healthcare personnel may more safely use and handle fluid substances including potentially hazardous liquids and the like.

SUMMARY

The present disclosure relates to components and systems for the transfer of a fluid/substance from a first container to a second container while maintaining a closed system.

According to an aspect of the present disclosure, a closed fluid transfer system for fluidly interconnecting a syringe to at least one of a patient I.V. set, a vial and an I.V. bag is provided. The closed fluid transfer system comprises a syringe adapter including a housing defining an open distal end and an open proximal end, the housing defining a pair of opposed longitudinally extending slots opening from the open distal end of the housing, the housing including a pair of opposed longitudinally extending ribs projecting from an inner surface thereof; a base supported in the open proximal end of the housing and including a luer connector; a collar slidably and rotatably supported in the housing, the collar defining a longitudinal opening therethrough, the collar defining a pair of opposed L-shaped tracks formed in an outer surface thereof and configured to receive a respective longitudinally extending rib therein, the collar defines a pair of opposed helical tracks opening from a distal surface of the collar, the opposed helical tracks being aligned with a respective slot of the housing when the collar is in a distal-most position; a shuttle slidably extending through longitudinal opening of the collar, the shuttle defining a lumen extending longitudinally therethrough; a barrel supported on and extending over a distal end of the shuttle, the barrel defining a central opening aligned with the lumen of the shuttle; a biasing member interposed between the collar and the shuttle for urging the collar away from the shuttle; a seal interposed between the shuttle and the barrel, wherein the seal extends across the lumen of the shuttle and the central opening of the barrel; and a needle defining a lumen therethrough, the needle having a proximal end supported in the base such that the lumen of the needle is in fluid communication with the luer connector, the needle having a sharpened distal tip disposed within the lumen of the shuttle when the shuttle is in a distal-most position.

The closed fluid transfer system further comprises another adapter for fluidly interconnecting the syringe adapter to one of the patient I.V. set, the vial and the I.V. bag. The another adapter includes a male stem for selectively connecting to and insertion into the open distal end of the syringe adapter, the male stem defining a lumen extending therethrough; a pair of opposed guide pins extending radially outward from the male stem; a pair of opposed guide surfaces extending radially outward from the male stem at a location proximal of the guide pins and being in registration with the guide pins; and a seal extending across the lumen of the male stem.

In use, the syringe adapter is movable from a closed state to an open state. In the closed state the tip of the needle is disposed within the lumen of the shuttle, the shuttle is disposed at the distal-most position, and the collar is disposed at a distal-most position.

The syringe adapter is movable from the closed state to the open state by inserting the guide pins of the male stem of the another adapter into the respective slots of the housing of the syringe adapter, whereby the seal of the another adapter abuts the seal of the syringe adapter; advancing the male stem of the another adapter into the open distal end of the housing such that the guide pins enter into the respective helical track of the collar to rotate the collar relative to the housing of the syringe and align the ribs of the housing with a through portion of the collar; and further advancing the male stem of the another adapter into the open distal end of the housing causes the collar to move proximally which causes the shuttle to move proximally until the tip of the needle penetrates through the abutting seals, whereby the syringe adapter is in the open state and fluidly interconnects the syringe with the another adapter.

Each seal may be made from polyisoprene.

The another adapter may be a vial adapter configured to fluidly interconnect the syringe adapter to the vial. The vial adapter includes a base defining an opening having a plurality of retainers extending around the opening of the base and being configured to snap-fit connect to a neck of the vial, the base defining a lower inner annular rim and an outer annular rim and a cavity therebetween; a cover supported on the outer rim of the base, wherein an expansion chamber is defined within the cover and the base; and an adapter support situated within the cavity of the base. The adapter support includes an annular flange for seating on the lower inner annular rim of the base and forming a fluid tight seal therebetween; an annular wall extending from the annular flange and defining an upper inner annular rim, wherein the cover is also supported on the upper inner annular rim; the male stem extending in a first direction from the annular flange; and a spike extending in a second direction from the annular flange, wherein the spike extends into the opening of the base, wherein the spike includes a first lumen being in fluid communication with the lumen of the male stem, and wherein the spike includes a second lumen being in fluid communication with the expansion chamber. The vial adapter further includes a bladder extending between the inner upper annular rim and the outer annular rim of the base.

The syringe adapter may be movable from the closed state to the open state by inserting the guide pins of the male stem of the vial adapter into the respective slots of the housing of the syringe adapter, whereby the seal of the vial adapter abuts the seal of the syringe adapter; advancing the male stem of the vial adapter into the open distal end of the housing such that the guide pins enter into the respective helical track of the collar to (1) rotate the collar relative to the housing of the syringe adapter and (2) align the ribs of the housing with a through portion of the collar; and further advancing the male stem of the vial adapter into the open distal end of the housing causing the collar to move proximally which causes the shuttle to move proximally until the tip of the needle penetrates through the abutting seals, whereby the syringe adapter is in the open state and fluidly interconnects the syringe with the vial adapter.

The spike of the vial adapter may penetrate a septum of the vial upon a connection of the base of the vial adapter to a neck of the vial.

When the syringe is connected to the syringe adapter, and when the syringe adapter is connected to the vial adapter, and when the vial adapter is connected to the vial, the syringe is in closed fluid communication with the vial.

When the syringe is connected to the syringe adapter, and when the syringe adapter is connected to the vial adapter, the tip of the needle of the syringe adapter penetrates the abutting seals of the syringe adapter and the vial adapter and when the vial adapter is connected to the vial, the syringe is in closed fluid communication with the vial.

In use, air from the syringe may be injectable into a cavity of the vial adapter defined between the bladder, and the base and the adapter support, through a fluid passage defined by the needle of the syringe adapter, the lumen of the male stem, the first lumen of the spike, the vial and the second lumen of the spike.

The another adapter may be a patient push adapter configured to fluidly interconnect the syringe adapter to the I.V. set. The patient push adapter includes a body portion having a the male stem disposed at a first end thereof and a patient push adapter luer connector at a second end thereof, wherein the patient push adapter luer connector is in fluid communication with the lumen of the male stem.

The syringe adapter is movable from the closed state to the open state by inserting the guide pins of the male stem of the patient push adapter into the respective slots of the housing of the syringe adapter, whereby the seal of the patient push adapter abuts the seal of the syringe adapter; advancing the male stem of the patient push adapter into the open distal end of the housing such that the guide pins enter into the respective helical track of the collar to rotate the collar relative to the housing of the syringe and align the ribs of the housing with a through portion of the collar; and further advancing the male stem of the patient push adapter into the open distal end of the housing causing the collar to move proximally which causes the shuttle to move proximally until the tip of the needle penetrates through the abutting seals, whereby the syringe adapter is in the open state and fluidly interconnects the syringe with the I.V. set.

When the syringe is connected to the syringe adapter, and when the syringe adapter is connected to the patient push adapter, the tip of the needle of the syringe adapter penetrates the abutting seals of the syringe adapter and the patient push adapter and when the patient push adapter is connected to the I.V. set, the syringe is in closed fluid communication with the I.V. set.

The another adapter may be an I.V. bag adapter configured to fluidly interconnect the syringe adapter to the I.V. bag. The I.V. bag adapter includes a body portion having a the male stem extending therefrom; a spike extending from a first end of the body portion, the spike defining a first lumen and a second lumen extending therethrough, wherein the first lumen of the spike is in fluid communication with the lumen of the male stem; an I.V. bag adapter luer connector disposed at a second end of the body portion and being in fluid communication with the second lumen of the spike.

The syringe adapter may be movable from the closed state to the open state by inserting the guide pins of the male stem of the I.V. bag adapter into the respective slots of the housing of the syringe adapter, whereby the seal of the I.V. bag adapter abuts the seal of the syringe adapter; advancing the male stem of the I.V. bag adapter into the open distal end of the housing such that the guide pins enter into the respective helical track of the collar to rotate the collar relative to the housing of the syringe and align the ribs of the housing with a through portion of the collar; and further advancing the male stem of the I.V. bag adapter into the open distal end of the housing causing the collar to move proximally which causes the shuttle to move proximally until the tip of the needle penetrates through the abutting seals, whereby the syringe adapter is in the open state and fluidly interconnects the syringe with the I.V. bag.

When the syringe is connected to the syringe adapter, and when the syringe adapter is connected to the I.V. bag adapter, the tip of the needle of the syringe adapter penetrates the abutting seals of the syringe adapter and the I.V. bag adapter and when the I.V. bag adapter is connected to the I.V. bag, the syringe is in closed fluid communication with the I.V. bag.

The syringe adapter may include a lock out system having a collar including at least one lock arm extending in a radial direction about the collar, wherein each lock arm includes a first end integral with the collar and a second free end defining a tooth extending radially outward and being dimensioned to contact a longitudinally extending rib of the housing; and a shuttle including a relatively larger diameter proximal portion and a relatively smaller diameter distal portion. When the shuttle is in the distal-most position, each lock arm is in registration with the relatively larger diameter portion of the shuttle thereby inhibiting each lock arm from deflecting radially inward. When the shuttle is moved proximally, the relatively smaller diameter portion of the shuttle is moved into registration with each lock arm thereby permitting each lock arm to deflect radially inward and to permit the collar to rotate.

According to another aspect of the present disclosure, a closed fluid transfer system for fluidly interconnecting a syringe to any one of a patient I.V. set, a vial and an I.V. bag. The closed fluid transfer system comprises a first adapter defining a first adapter lumen extending therethrough, the first adapter supporting a first adapter seal extending across a first end of the first adapter lumen and a first adapter luer connector at a second end of the first adapter lumen for selectively connecting the first adapter to the syringe, the first adapter supporting a rear end of a needle within the first adapter lumen, wherein the first adapter seal is movable relative to a tip of the needle such that the tip of the needle penetrates through the first adapter seal.

The closed fluid transfer system further comprises at least one second adapter for fluidly interconnecting the first adapter to one of the patient I.V. set, the vial and the I.V. bag, the at least one second adapter defining a second adapter lumen extending therethrough, the at least one second adapter supporting a second adapter seal extending across a first end of the second adapter lumen and a connector at a second end of the second adapter lumen for selectively connecting the second adapter to one of the patient I.V. set, the vial and the I.V. bag.

When the at least one second adapter is coupled to the first adapter, the second adapter seal abuts the first adapter seal and moves the first adapter seal relative to the tip of the needle such that the tip of the needle penetrates through the abutting first adapter seal and second adapter seal.

The first adapter may include a housing defining an open distal end and an open proximal end, the housing defining a pair of opposed longitudinally extending slots opening from the open distal end of the housing, the housing including a pair of opposed longitudinally extending ribs projecting from an inner surface thereof; a base supported in the open proximal end of the housing and including the first adapter luer connector; a collar slidably and rotatably supported in the housing, the collar defining a longitudinal opening therethrough, the collar defining a pair of opposed L-shaped tracks formed in an outer surface thereof and configured to receive a respective longitudinally extending rib therein, the collar defines a pair of opposed helical tracks opening from a distal surface of the collar, the opposed helical tracks being aligned with a respective slot of the housing when the collar is in a distal-most position; a shuttle slidably extending through longitudinal opening of the collar, the shuttle defining a shuttle lumen extending longitudinally therethrough; a barrel supported on and extending over a distal end of the shuttle, the barrel defining a central opening aligned with the shuttle lumen; and a biasing member interposed between the collar and the shuttle for urging the collar away from the shuttle.

The first adapter seal may be interposed between the shuttle and the barrel, wherein the first adapter seal extends across the shuttle lumen and the central opening of the barrel. The tip of the needle may be disposed within the shuttle lumen when the shuttle is in a distal-most position.

The at least one second adapter may include a second adapter male stem for selectively connecting to and insertion into the open distal end of the first adapter, the second adapter male stem defining the second adapter lumen; a pair of opposed guide pins extending radially outward from the male stem; and a pair of opposed guide surfaces extending radially outward from the male stem at a location proximal of the guide pins and being in registration with the guide pins.

The second adapter seal may extend across the second adapter lumen.

The first adapter may be movable from a closed state to an open state. In the closed state the tip of the needle is disposed within the shuttle lumen, the shuttle is disposed at the distal-most position, and the collar is disposed at a distal-most position. The first adapter is movable from the closed state to the open state by inserting the guide pins of the second adapter male stem into the respective slots of the housing of the first adapter, whereby the second adapter seal of the second adapter abuts the first adapter seal of the first adapter; advancing the second adapter male stem into the open distal end of the housing such that the guide pins of the second adapter enter into the respective helical track of the collar to (1) rotate the collar relative to the housing of the first adapter and (2) align the ribs of the housing with a through portion of the collar; and further advancing the second adapter male stem into the open distal end of the housing causing the collar to move proximally which causes the shuttle to move proximally until the tip of the needle penetrates through the abutting seals, whereby the first adapter is in the open state and fluidly interconnects the syringe with the second adapter.

The at least one second adapter may include a third adapter. The third adapter includes a base defining an opening having a plurality of retainers extending around the opening of the base and being configured to snap-fit connect to a neck of the vial, the base defining a lower inner annular rim and an outer annular rim and a cavity therebetween; a cover supported on the outer rim of the base, wherein an expansion chamber is defined within the cover and the base; and an adapter support situated within the cavity of the base. The adapter support includes an annular flange for seating on the lower inner annular rim of the base and forming a fluid tight seal therebetween; an annular wall extending from the annular flange and defining an upper inner annular rim, wherein the cover is also supported on the upper inner annular rim; a third adapter male stem for selectively connecting to and insertion into the open distal end of the first adapter, the third adapter male stem defining a third adapter lumen, the third adapter male stem extending in a first direction from the annular flange; a pair of opposed guide pins extending radially outward from the third adapter male stem; and a pair of opposed guide surfaces extending radially outward from the third adapter male stem at a location proximal of the guide pins and being in registration with the guide pins; a third adapter seal extending across the third adapter lumen; and a spike extending in a second direction from the annular flange, wherein the spike extends into the opening of the base, wherein the spike includes a first spike lumen being in fluid communication with the lumen of the male stem of the third adapter, and wherein the spike includes a second spike lumen being in fluid communication with the expansion chamber. The third adapter further includes a bladder extending between the inner upper annular rim and the outer annular rim of the base.

The first adapter is movable from the closed state to the open state by inserting the guide pins of the third adapter male stem into the respective slots of the housing of the first adapter, whereby the third adapter seal of the third adapter abuts the first adapter seal of the first adapter; advancing the third adapter male stem into the open distal end of the housing such that the guide pins of the third adapter enter into the respective helical track of the collar to (1) rotate the collar relative to the housing of the first adapter and (2) align the ribs of the housing with a through portion of the collar; and further advancing the third adapter male stem into the open distal end of the housing causing the collar to move proximally which causes the shuttle to move proximally until the tip of the needle penetrates through the abutting seals, whereby the first adapter is in the open state and fluidly interconnects the syringe with the third adapter.

The spike of the third adapter penetrates a septum of the vial upon a connection of the base of the third adapter to a neck of the vial.

When the syringe is connected to the first adapter, and when the first adapter is connected to the third adapter, and when the third adapter is connected to the vial, the syringe is in closed fluid communication with the vial.

When the syringe is connected to the first adapter, and when the first adapter is connected to the third adapter, the tip of the needle of the first adapter penetrates the abutting seals of the first adapter and the third adapter and when the third adapter is connected to the vial, the syringe is in closed fluid communication with the vial.

The at least one second adapter includes a fourth adapter configured to fluidly interconnect the first adapter to the I.V. bag. The fourth adapter includes a body portion having a fourth adapter male stem disposed at a first end thereof and a fourth adapter luer connector extending therefrom; a pair of opposed guide pins extending radially outward from the fourth adapter male stem; a pair of opposed guide surfaces extending radially outward from the fourth adapter male stem at a location proximal of the guide pins and being in registration with the guide pins; a fourth adapter seal extending across the fourth adapter lumen; a spike extending from a second end of the body portion, the spike defining a first lumen and a second lumen extending therethrough.

The first lumen of the spike is in fluid communication with a lumen of the fourth adapter male stem, and the second lumen of the spike is in fluid communication with a lumen of the fourth adapter luer.

The first adapter is movable from the closed state to the open state by inserting the guide pins of the fourth adapter male stem into the respective slots of the housing of the first adapter, whereby the fourth adapter seal adapter abuts the first adapter seal; advancing the fourth adapter male stem into the open distal end of the housing such that the guide pins of the fourth adapter enter into the respective helical track of the collar to (1) rotate the collar relative to the housing of the first adapter and (2) align the ribs of the housing with a through portion of the collar; and further advancing the fourth adapter male stem into the open distal end of the housing causing the collar to move proximally which causes the shuttle to move proximally until the tip of the needle penetrates through the abutting seals, whereby the first adapter is in the open state and fluidly interconnects the syringe with the fourth adapter.

When the syringe is connected to the first adapter, and when the first adapter is connected to the second adapter, the tip of the needle of the first adapter penetrates the abutting seals of the first adapter and the second adapter and when the second adapter is connected to the I.V. bag, the syringe is in closed fluid communication with the I.V. bag.

The first adapter includes a lock out system having a collar including at least one lock arm extending in a radial direction about the collar, wherein each lock arm includes a first end integral with the collar and a second free end defining a tooth extending radially outward and being dimensioned to contact a longitudinally extending rib of the housing; and a shuttle including a relatively larger diameter proximal portion and a relatively smaller diameter distal portion.

When the shuttle is in the distal-most position, each lock arm is in registration with the relatively larger diameter portion of the shuttle thereby inhibiting each lock arm from deflecting radially inward. When the shuttle is moved proximally, the relatively smaller diameter portion of the shuttle is moved into registration with each lock arm thereby permitting each lock arm to deflect radially inward and to permit the collar to rotate.

According to yet another aspect of the present disclosure, a syringe adapter for a closed fluid transfer system is provided. The syringe adapter includes a housing defining an open distal end and an open proximal end, the housing defining a pair of opposed longitudinally extending slots opening from the open distal end of the housing, the housing including a pair of opposed longitudinally extending ribs projecting from an inner surface thereof; a base supported in the open proximal end of the housing and including the syringe adapter luer connector; a collar slidably and rotatably supported in the housing, the collar defining a longitudinal opening therethrough, the collar defining a pair of opposed L-shaped tracks formed in an outer surface thereof and configured to receive a respective longitudinally extending rib therein, the collar defines a pair of opposed helical tracks opening from a distal surface of the collar, the opposed helical tracks being aligned with a respective slot of the housing when the collar is in a distal-most position; a shuttle slidably extending through longitudinal opening of the collar, the shuttle defining a shuttle lumen extending longitudinally therethrough; a barrel supported on and extending over a distal end of the shuttle, the barrel defining a central opening aligned with the shuttle lumen; and a biasing member interposed between the collar and the shuttle for urging the collar away from the shuttle.

The syringe adapter seal is interposed between the shuttle and the barrel, wherein the syringe first adapter seal extends across the shuttle lumen and the central opening of the barrel. The tip of the needle is disposed within the shuttle lumen when the shuttle is in a distal-most position.

The syringe adapter may be movable from a closed state to an open state; wherein in the closed state the tip of the needle is disposed within the shuttle lumen, the shuttle is disposed at the distal-most position, and the collar is disposed at a distal-most position.

Wherein the syringe adapter is movable from the closed state to the open state by inserting a pair of opposed radially extending guide pins of a male stem of a second adapter into the respective slots of the housing of the syringe adapter, whereby a second adapter seal of the second adapter abuts the first adapter seal of the first adapter; advancing the second adapter male stem into the open distal end of the housing such that the guide pins of the second adapter enter into the respective helical track of the collar to (1) rotate the collar relative to the housing of the syringe adapter and (2) align the ribs of the housing with a through portion of the collar; and further advancing the second adapter male stem into the open distal end of the housing causing the collar to move proximally which causes the shuttle to move proximally until the tip of the needle penetrates through the abutting seals, whereby the syringe adapter is in the open state and fluidly interconnects a syringe with the second adapter.

According to still another aspect of the present disclosure, a vial adapter for a closed fluid transfer system is provided. The vial adapter includes a base defining an opening having a plurality of retainers extending around the opening of the base and being configured to snap-fit connect to a neck of a vial, the base defining a lower inner annular rim and an outer annular rim and a cavity therebetween; a cover supported on the outer rim of the base, wherein an expansion chamber is defined within the cover and the base; and an adapter support situated within the cavity of the base. The adapter support includes an annular flange for seating on the lower inner annular rim of the base and forming a fluid tight seal therebetween; an annular wall extending from the annular flange and defining an upper inner annular rim, wherein the cover is also supported on the upper inner annular rim; a male stem extending in a first direction from the annular flange; a male stem for selectively connecting to and insertion into a open distal end of a syringe adapter, the male stem defining a lumen extending therethrough; a pair of opposed guide pins extending radially outward from the male stem; a pair of opposed guide surfaces extending radially outward from the male stem at a location proximal of the guide pins and being in registration with the guide pins; a seal extending across the lumen of the male stem; and a spike extending in a second direction from the annular flange, wherein the spike extends into the opening of the base, wherein the spike includes a first lumen being in fluid communication with the lumen of the male stem, and wherein the spike includes a second lumen being in fluid communication with the expansion chamber. The vial adapter further includes a bladder extending between the inner upper annular rim and the outer annular rim of the base.

The vial adapter is configured to move a syringe adapter from a closed state to an open state. The syringe adapter includes a housing defining an open distal end and an open proximal end, the housing defining a pair of opposed longitudinally extending slots opening from the open distal end of the housing, the housing including a pair of opposed longitudinally extending ribs projecting from an inner surface thereof; a base supported in the open proximal end of the housing and including the syringe adapter luer connector; a collar slidably and rotatably supported in the housing, the collar defining a longitudinal opening therethrough, the collar defining a pair of opposed L-shaped tracks formed in an outer surface thereof and configured to receive a respective longitudinally extending rib therein, the collar defines a pair of opposed helical tracks opening from a distal surface of the collar, the opposed helical tracks being aligned with a respective slot of the housing when the collar is in a distal-most position; a shuttle slidably extending through longitudinal opening of the collar, the shuttle defining a shuttle lumen extending longitudinally therethrough; a barrel supported on and extending over a distal end of the shuttle, the barrel defining a central opening aligned with the shuttle lumen; and a biasing member interposed between the collar and the shuttle for urging the collar away from the shuttle. The syringe adapter seal is interposed between the shuttle and the barrel, wherein the syringe first adapter seal extends across the shuttle lumen and the central opening of the barrel. The tip of the needle is disposed within the shuttle lumen when the shuttle is in a distal-most position.

In use, the vial adapter moves the syringe adapter from the closed state to the open state upon inserting the guide pins of the male stem of the vial adapter into the respective slots of the housing of the syringe adapter, whereby the seal of the vial adapter abuts the seal of the syringe adapter; advancing the male stem of the vial adapter into the open distal end of the housing such that the guide pins enter into the respective helical track of the collar to (1) rotate the collar relative to the housing of the syringe adapter and (2) align the ribs of the housing with a through portion of the collar; and further advancing the male stem of the vial adapter into the open distal end of the housing causing the collar to move proximally which causes the shuttle to move proximally until the tip of the needle penetrates through the abutting seals, whereby the syringe adapter is in the open state and fluidly interconnects the syringe with the vial adapter.

According to yet another aspect of the present disclosure, a patient push adapter for a closed fluid transfer system is provided. The patient push adapter includes a body portion having a male stem disposed at a first end thereof and a patient push adapter luer connector at a second end thereof, wherein the male stem defines a lumen extending therethrough and wherein the patient push adapter luer connector is in fluid communication with the lumen of the male stem; a pair of opposed guide pins extending radially outward from the male stem; a pair of opposed guide surfaces extending radially outward from the male stem at a location proximal of the guide pins and being in registration with the guide pins; and a seal extending across the lumen of the male stem.

The patient push adapter is configured to move a syringe adapter from a closed state to an open state. The syringe adapter includes a housing defining an open distal end and an open proximal end, the housing defining a pair of opposed longitudinally extending slots opening from the open distal end of the housing, the housing including a pair of opposed longitudinally extending ribs projecting from an inner surface thereof; a base supported in the open proximal end of the housing and including the syringe adapter luer connector; a collar slidably and rotatably supported in the housing, the collar defining a longitudinal opening therethrough, the collar defining a pair of opposed L-shaped tracks formed in an outer surface thereof and configured to receive a respective longitudinally extending rib therein, the collar defines a pair of opposed helical tracks opening from a distal surface of the collar, the opposed helical tracks being aligned with a respective slot of the housing when the collar is in a distal-most position; a shuttle slidably extending through longitudinal opening of the collar, the shuttle defining a shuttle lumen extending longitudinally therethrough; a barrel supported on and extending over a distal end of the shuttle, the barrel defining a central opening aligned with the shuttle lumen; and a biasing member interposed between the collar and the shuttle for urging the collar away from the shuttle. The syringe adapter seal is interposed between the shuttle and the barrel, wherein the syringe first adapter seal extends across the shuttle lumen and the central opening of the barrel. The tip of the needle is disposed within the shuttle lumen when the shuttle is in a distal-most position.

In use, the patient push adapter moves the syringe adapter from the closed state to the open state upon inserting the guide pins of the male stem of the patient push adapter into the respective slots of the housing of the syringe adapter, whereby the seal of the patient push adapter abuts the seal of the syringe adapter; advancing the male stem of the patient push adapter into the open distal end of the housing such that the guide pins enter into the respective helical track of the collar to (1) rotate the collar relative to the housing of the syringe adapter and (2) align the ribs of the housing with a through portion of the collar; and further advancing the male stem of the patient push adapter into the open distal end of the housing causing the collar to move proximally which causes the shuttle to move proximally until the tip of the needle penetrates through the abutting seals, whereby the syringe adapter is in the open state and fluidly interconnects the syringe with the patient push adapter.

According to a further aspect of the present disclosure, an I.V. bag adapter for a closed fluid transfer system is provided. The I.V. bag adapter includes a body portion having a the male stem extending therefrom; a body portion having a male stem extending from a side thereof, wherein the male stem defines a lumen extending therethrough; a pair of opposed guide pins extending radially outward from the male stem; a pair of opposed guide surfaces extending radially outward from the male stem at a location proximal of the guide pins and being in registration with the guide pins; a seal extending across the lumen of the male stem; a spike extending from a first end of the body portion, the spike defining a first lumen and a second lumen extending therethrough, wherein the first lumen of the spike is in fluid communication with the lumen of the male stem; and an I.V. bag adapter luer connector disposed at a second end of the body portion and being in fluid communication with the second lumen of the spike.

The I.V. bag adapter is configured to move a syringe adapter from a closed state to an open state. The syringe adapter includes a housing defining an open distal end and an open proximal end, the housing defining a pair of opposed longitudinally extending slots opening from the open distal end of the housing, the housing including a pair of opposed longitudinally extending ribs projecting from an inner surface thereof; a base supported in the open proximal end of the housing and including the syringe adapter luer connector; a collar slidably and rotatably supported in the housing, the collar defining a longitudinal opening therethrough, the collar defining a pair of opposed L-shaped tracks formed in an outer surface thereof and configured to receive a respective longitudinally extending rib therein, the collar defines a pair of opposed helical tracks opening from a distal surface of the collar, the opposed helical tracks being aligned with a respective slot of the housing when the collar is in a distal-most position; a shuttle slidably extending through longitudinal opening of the collar, the shuttle defining a shuttle lumen extending longitudinally therethrough; a barrel supported on and extending over a distal end of the shuttle, the barrel defining a central opening aligned with the shuttle lumen; and a biasing member interposed between the collar and the shuttle for urging the collar away from the shuttle. The syringe adapter seal being interposed between the shuttle and the barrel, wherein the syringe first adapter seal extends across the shuttle lumen and the central opening of the barrel. The tip of the needle being disposed within the shuttle lumen when the shuttle is in a distal-most position.

In use, the I.V. bag adapter moves the syringe adapter from the closed state to the open state upon inserting the guide pins of the male stem of the I.V. bag adapter into the respective slots of the housing of the syringe adapter, whereby the seal of the I.V. bag adapter abuts the seal of the syringe adapter; advancing the male stem of the I.V. bag adapter into the open distal end of the housing such that the guide pins enter into the respective helical track of the collar to (1) rotate the collar relative to the housing of the syringe adapter and (2) align the ribs of the housing with a through portion of the collar; and further advancing the male stem of the I.V. bag adapter into the open distal end of the housing causing the collar to move proximally which causes the shuttle to move proximally until the tip of the needle penetrates through the abutting seals, whereby the syringe adapter is in the open state and fluidly interconnects the syringe with the I.V. bag adapter.

The invention will be explained in greater detail below in descriptions of preferred embodiments and referring to the attached figures.

BRIEF DESCRIPTION OF THE DRAWINGS

In the following, the preferred embodiments of invention will be described in detail with reference to the following attached figures:

FIG. 19 is a further side, elevational view of a distal end of the syringe adapter of FIG. 17;

FIG. 20 is a longitudinal, cross-sectional view of a distal end of the syringe adapter of FIGS. 17-19;

FIG. 28 is a schematic, elevational view of the universal vial adapter of FIG. 25, shown connected to a vial neck having a second diameter;

FIG. 29 is a top, plan view of a hub of the universal vial adapter as connected to the vial of FIG. 28;

FIG. 30 is a perspective view of the hub of the universal vial adapter as connected to the vial of FIG. 28;

DETAILED DESCRIPTION

Figure 1:
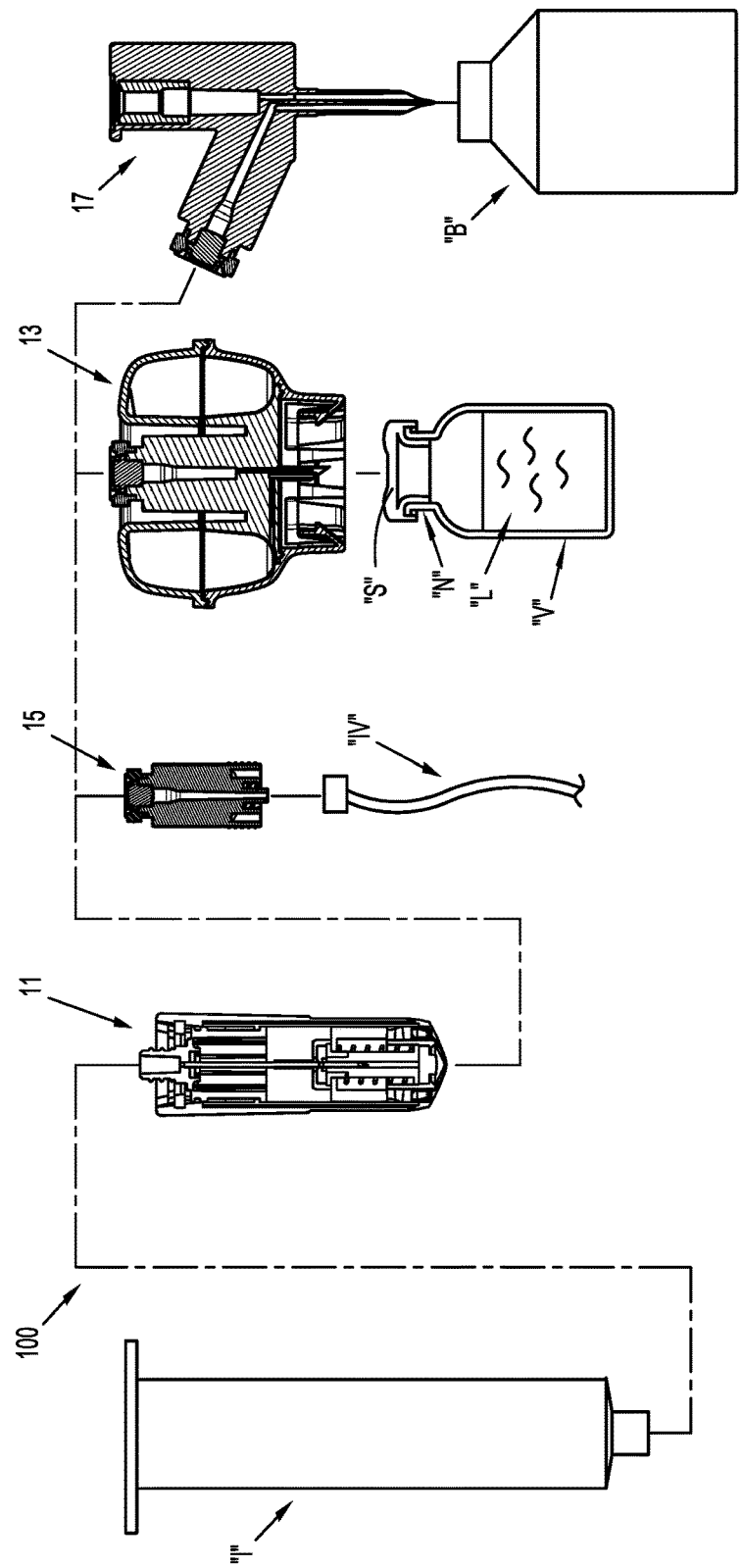
FIG. 1 is a schematic illustration of a closed fluid transfer system of the present disclosure illustrating a fluid connectability of a syringe to an I.V. Set, a vial and an I.V. bag via combination of a syringe adapter and one of an I.V. set adapter, a vial adapter and an I.V. bag adapter.
Figure 2:
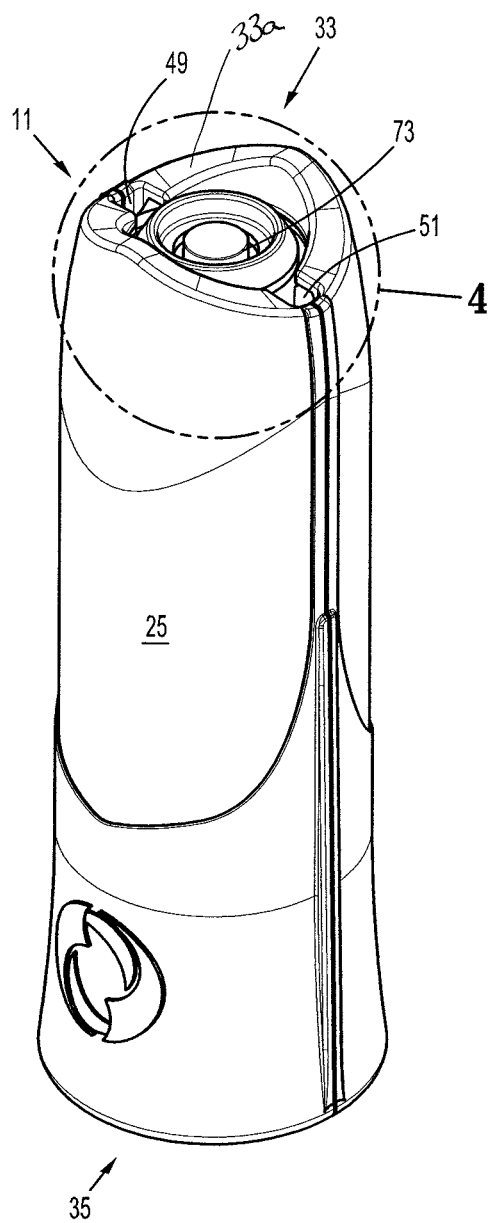
FIG. 2 is a perspective view of a syringe adapter of the closed fluid transfer system of FIG. 1.

The closed fluid transfer system, in accordance with the present disclosure, is generally designated as 100 and generally includes a module/adapter that fluidly connects to a syringe or any male luer lock connection point; a patient push module/adapter that fluidly connects directly to an I.V. line; at least a module/adapter that fluidly connects to a vial/container storing/containing a fluid/liquid in the form of a hazardous drug and the like; and a module/adapter that fluidly connects to an I.V. bag. Each of the above-mentioned modules/adapters will be described in greater detail below with reference to the accompanying figures, wherein like numbers identify like elements.

In accordance with the present disclosure, the system is a "closed" fluid-transfer system capable of transferring liquids between a conventional syringe and one of a patient I.V. set, a vial, or an I.V. bag without leaking or spilling and without exposure of the gases/fluids/liquids or other substances to a location or a substance outside the closed system. One purpose of the closed fluid transfer system is to permit health care personnel to safely use and handle liquid-form medicine, including potentially hazardous liquid drugs and/or the like.

In accordance with the present disclosure, and as will be discussed in greater detail below, the closed fluid transfer system 100 includes a syringe adapter 11 (see FIGS. 1-7) that is structured to provide a closed fluid connection between a first fluid container in the form of a conventional needleless syringe "I" and a second fluid container/conduit in the form of a patient I.V. set, a vial "V", or an I.V. bag. The fluid transfer is accomplished by first connecting one of a patient push adapter 15 (see FIGS. 1 and 11-14) to an I.V. set, a vial adapter 13 (see FIGS. 1 and 8-10) to a vial, or an I.V. bag adapter 17 (see FIGS. 1 and 15-16) to an I.V. bag, as necessary. Each adapter 13, 15, 17 is provided with an identical male stem 19 which defines an internal lumen 21 closed at one end by a resilient seal 23. The syringe adapter 11 is mated to the male stem 19, thereby permitting fluid flow from or to the syringe "I", as described in more detail herein.

Referring now specifically to FIGS. 1-7, the closed fluid transfer system 100 includes a syringe adapter 11. Syringe adapter 11 is a type of valve which can be in an open state to permit fluid flow therethrough or in a closed state to prevent fluid flow. The open and closed states occur in a specific sequence dictated by the syringe adapter 11 architecture as described herein.

The syringe adapter 11 consists of four main parts which are a housing 25, a conventional hollow metal needle 27, a shuttle 29, and a collar 31. The housing 25 is generally cylindrical in shape having a distal end 33 and a proximal end 35, a longitudinal axis 37, a distal opening 39, and a female cavity 41 into which the male stem 19 is received. Housing 25 may be formed to have two housing side portions or halves 43, 45 and a housing base portion 47 which fits partially between the side portions 43, 45. Side portions 43, 45 define opposed slots 49, 51 (see FIGS. 2 and 4) which begin at housing distal end 33 and extend within housing 25. Slots 49, 51 which receive a respective guide pin 53, 55 and guide surface 57, 59 of any male stem 19, which are each keyed to a respective one of the slots 49, 51 (or a respective one of slots 51, 49), for the purposes described in full detail below.

Figure 3:
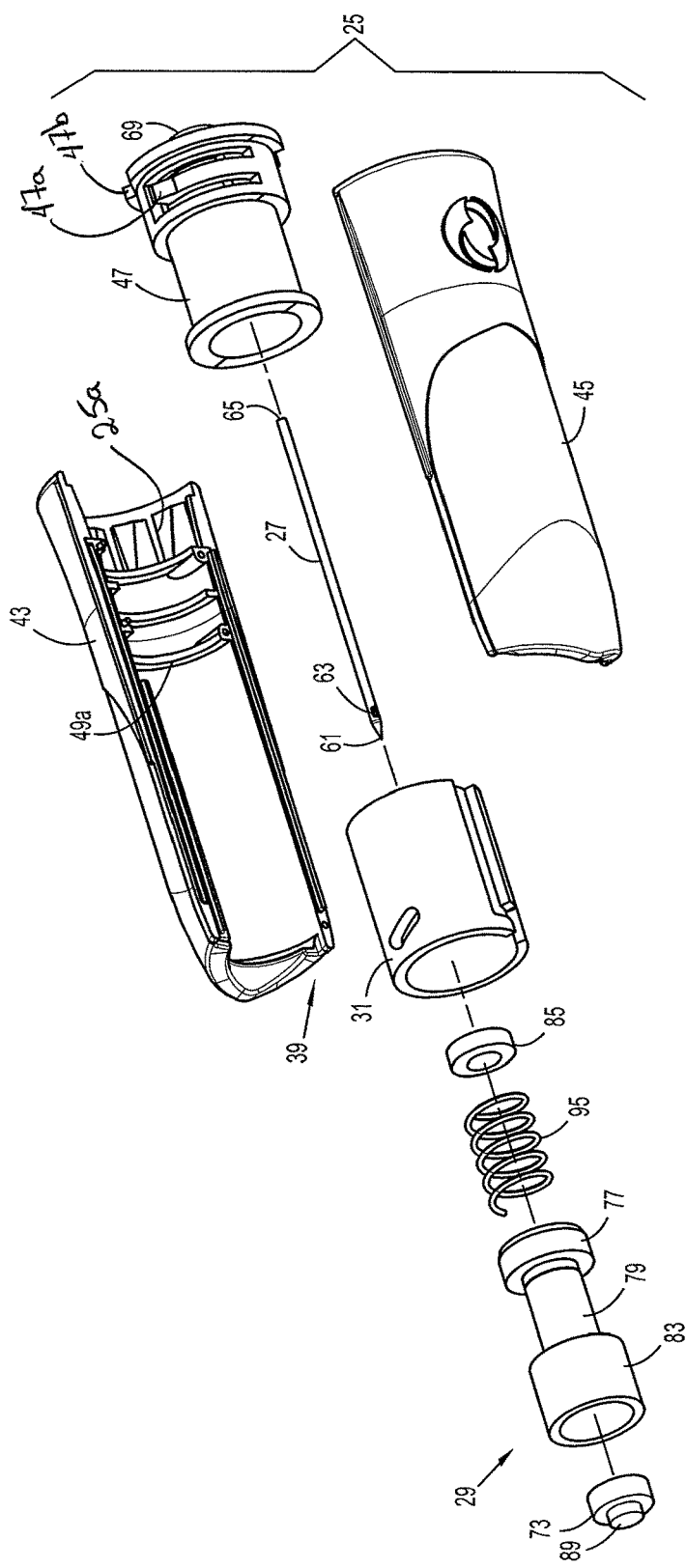
FIG. 3 is a perspective view, with parts separated, of the syringe adapter of FIG. 2.
Figure 4:
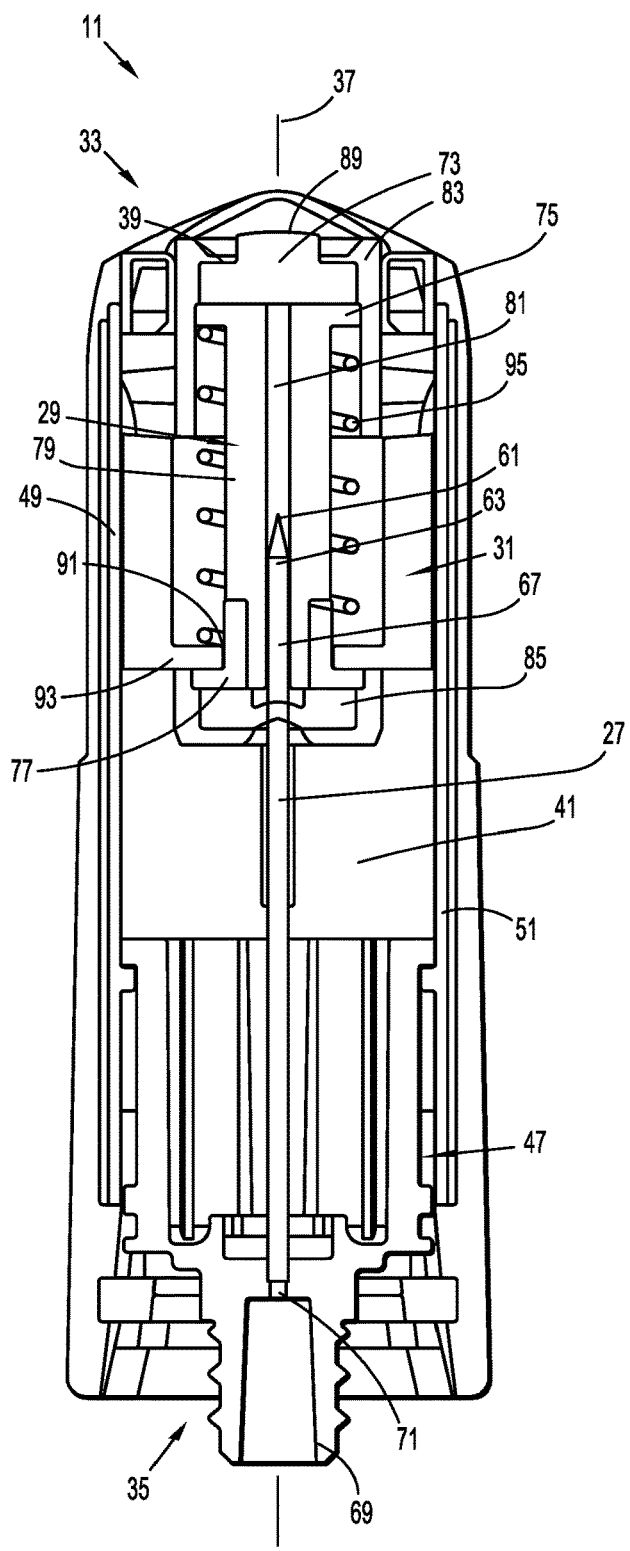
FIG. 4 is a longitudinal, cross-sectional view of the syringe adapter of FIGS. 2 and 3.

Hollow metal needle 27, as seen in FIGS. 3 and 4, is a conventional needle with a sharpened tip 61, a tip end opening 63, a proximal end opening 65, and a lumen 67 permitting fluid flow through the conventional needle 27 between the needle openings 63, 65. It is envisioned that needle 27 will be a conventional 18 gauge steel "pencil tip" needle commercially available (18 gauge refers to the outer diameter of needle 27). The conventional pencil tip needle 27 has an extremely sharp tip 61 with opening 63 spaced slightly away from the sharpened tip 61. The pencil tip needle 27 is of a type and size conventionally used with syringes to penetrate patient blood vessels for delivery or extraction of fluids.

Needle 27 is mounted within housing 25, in fixed-positional relationship, on an inner side of base 47 with tip 61 of needle 27 pointing/extending toward distal end 33 of housing 25. An advantage of this design is that needle 27, and specifically, the extremely sharp needle tip 61 of needle 27, are fully enclosed within the housing 25 and are completely shielded from contact with a user. In this manner, the possibility of injuries as a result of user needle-stick, has been significantly reduced and/or eliminated.

Housing base 47 is rotatably supported in housing 25. Housing base 47 includes an outer side with a conventional luer connector 69 provided to accept the delivery end of a conventional needleless syringe. A lumen 71 extends through base 47 between luer connector 69 and proximal opening 65 of needle 27 permitting fluid flow between the needle tip opening 63 and the luer connector 69.

Housing 25 and housing base 47 of syringe adapter 11 cooperate with one another to provide a ratchet mechanism by which syringe adapter 11 may not be accidentally or inadvertently disconnected from syringe "I". In particular, the ratchet mechanism includes, as seen in FIG. 3, a plurality of ribs 25a formed on an inner surface of housing 25 and at least one resilient finger 47a supported on housing base 47, whereby housing base 47 is held in a fixed position relative to housing 25 when syringe adapter 11 is connected to syringe "I" and to is free to rotate relative to housing 25 if syringe adapter 11 is being inadvertently or accidently disconnected from syringe "I". In this manner, the closed system between the syringe adapter 11 and syringe "I" is better maintained.

Generally, in operation, when syringe adapter 11 is connected to syringe "I", the at least one resilient finger 47a of housing base 47 engages ribs 25a of housing in such a manner that rotation of housing base 47 relative to housing 25 is inhibited and syringe adapter 11 may be securely connected to syringe "I". Further, if there is an inadvertent or accidental rotation of syringe adapter 11 relative to syringe "I", tending to disconnect syringe adapter 11 from syringe "I", and thus destroy the closed system, each resilient finger 47a is configured to slip over and across ribs 25a of housing 25, allowing housing base 47 to rotate relative to housing 25 and thus maintain the closed system.

If it is desired to intentionally disconnect syringe "I" from syringe adapter 11, a user may squeeze housing 25 radially inward, in the proximity of luer connector 69, to engage at least one tooth (not shown) formed on an inner surface of housing 25 with a respective notch 47b formed in an outer surface of housing base 47. Then, with the at least one tooth (not shown) of housing 25 engaged with the respective notch 47b of housing base 47, the user may rotate syringe adapter 11 relative to syringe "I" to disconnect syringe "I" from luer connector 69 of housing base 47.

Shuttle 29 is provided for at least the following important purposes. First, shuttle 29 supports shuttle distal seal 73 across distal opening 39 of housing 25 to close cavity 41 of housing 25 so that contaminants cannot enter the housing 25 when the syringe adapter 11 is not mated to one of the adapters 13, 15, 17. Second, the shuttle 29 supports shuttle distal seal 73 at a position across distal opening 39 of housing 25 so that distal seal 73 can be easily swabbed with alcohol before use to ensure that the seal 73 is sterile. In accordance with the present disclosure, and as is customary, a seal 23 of any male stem 19 (as seen in for example FIG. 8 and as will be described in greater detail below) is also swabbed with alcohol or other microbial agent before being mated to the syringe adapter 11, so as to ensure sterility of the abutment between seals 23 and 73. Finally, the shuttle 29 provides a fluid-tight enclosure for needle 27 to prevent fluid flow outside of syringe adapter 11 when in the closed state.

As illustrated in FIGS. 3 and 4, shuttle 29 includes distal and proximal annular flanges 75, 77, respectively, and an intermediate body portion 79 between flanges 75, 77 defining a shuttle lumen 81 therethrough. Distal flange 75 supports a distal seal 73 and a barrel 83, seated on distal flange 75, holds distal seal 73 on distal flange 75. Shuttle proximal flange 77 supports a proximal seal 85.

As illustrated in FIGS. 3 and 4, tip 61 of needle 27 extends into shuttle lumen 81 and proximal seal 85 forms a fluid-tight seal around needle 27. In the closed state, when syringe adapter 11 is fluidly connected to syringe "I", needle tip 61 and opening 63 are within shuttle lumen 81 and seals 73, 85 prevent fluid from exiting shuttle lumen 81.

Each seal 23, 73 is generally disk shaped and includes a respective outward projection 87, 89 (i.e., convex surface) which abut one another when the seals 23, 73 are held together, as described later herein. Seals 23, 73 and 85 are made of polyisoprene and seals 23 and 73 are designed to retain or return to their original convex profile when in abutment with one another. Put another way, since seals 23, 73 are fabricated from a resilient material and tend to want to retain or return to their original convex profile, when seals 23, 73 are in abutment with one another, a substantially continuous interface between seals 23, 73 is established and maintained. While it is preferred that seals 23 and 73 be made from polyisoprene, it is contemplated and within the scope of the present disclosure, that seals 23, 73 may be made from thermoplastic elastomers (TPE), silicone, more specifically, HaloButyl-Polyisoprene, Chlorobutyl, thermoplastic vulcanizates (TPVs), any other resilient polymer, or any combinations thereof.

Intermediate portion 79 of shuttle 29 rides in collar opening 91 in collar end wall 93 of collar 31 for axial movement along axis 37 within housing 25. Barrel 83 is generally cylindrical in shape and has an outside diameter slightly less than an inside diameter of collar 31 to permit barrel 83 and shuttle 29 to reciprocate inside collar 31.

A spring 95 is provided and bears against end wall 93 of collar 31 and distal flange 75, partially within barrel 83. Spring 95 biases shuttle 29 toward distal end 33 of housing 25 so that distal seal 73 of shuttle 29 covers or extends across opening 39 of housing 25, for the reasons previously described. Spring-biased contact between barrel 83 and end wall 93 of collar 31 limits inward movement of shuttle 29 toward proximal end 35 of housing 25, and contact between proximal flange 77 of shuttle 29 and end wall 93 of collar 31 limits outward movement of shuttle 29 toward distal end 33 of housing 25.

Distal seal 73 of shuttle 29 does not contact the housing 25 and is supported solely by shuttle 29 and travels within collar 31 spaced from housing 25. Shuttle 29 is pushed axially toward proximal end 35 of housing 25 when contacted by seal 23 of any male stem 19 during use, as described more fully below.

Figure 8:
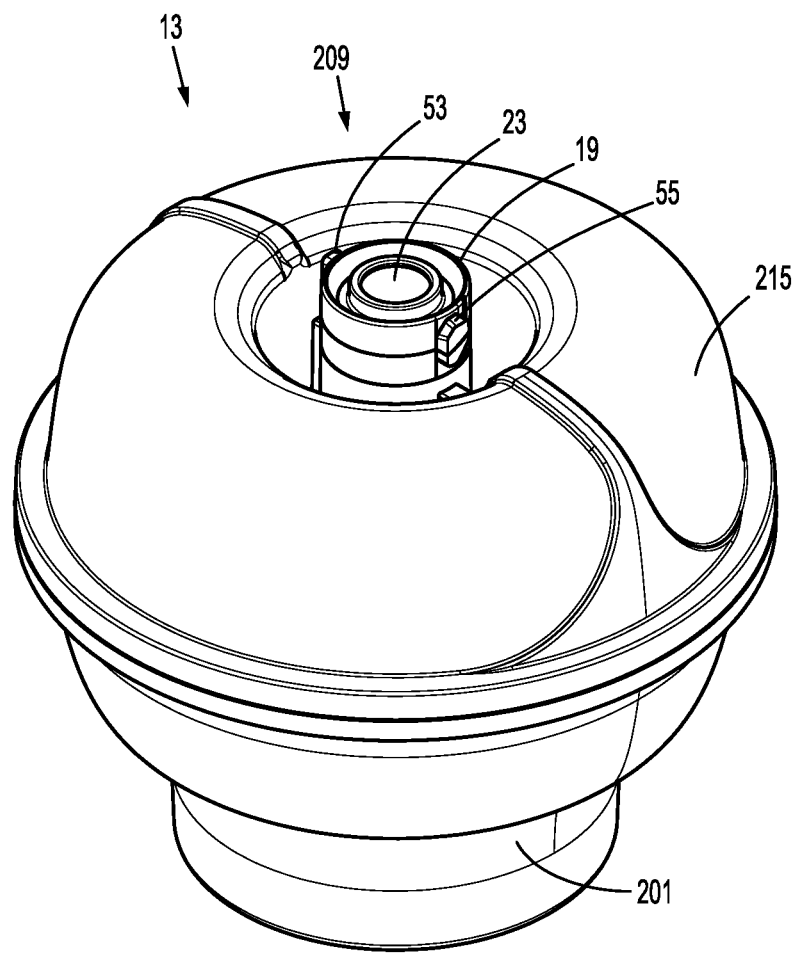
FIG. 8 is a perspective view of a vial adapter of the closed fluid transfer system of FIG. 1.

With continued reference to FIGS. 2-7, collar 31 and housing 25 cooperate to hold male stem 19 and seal 23 (for example, as seen in FIG. 8) thereof in abutment with distal seal 73 of shuttle 29 so that the abutting seals 23, 73 can subsequently be pierced by needle tip 61 of needle 27 and so that needle 27 can enter lumen 21 of male stem 19 to open the fluid path through syringe adapter 11. The abutment between seals 23, 73 established that distal seal 73 of shuttle 29 is the closure for distal opening 39 of housing 25 and also places distal seal 73 of shuttle 29 in a position convenient for swabbing with alcohol before use. The abutment between seals 23, 73 ensures that the two seals 23, 73 function as one and can be pierced together by needle 27. If the seals 23, 73 were to separate with needle tip opening 63 extended outside of lumen 81 of shuttle 29, liquids could leak into cavity 41 of housing 25, which is contrary to the purpose of providing a closed system.

Figure 5:
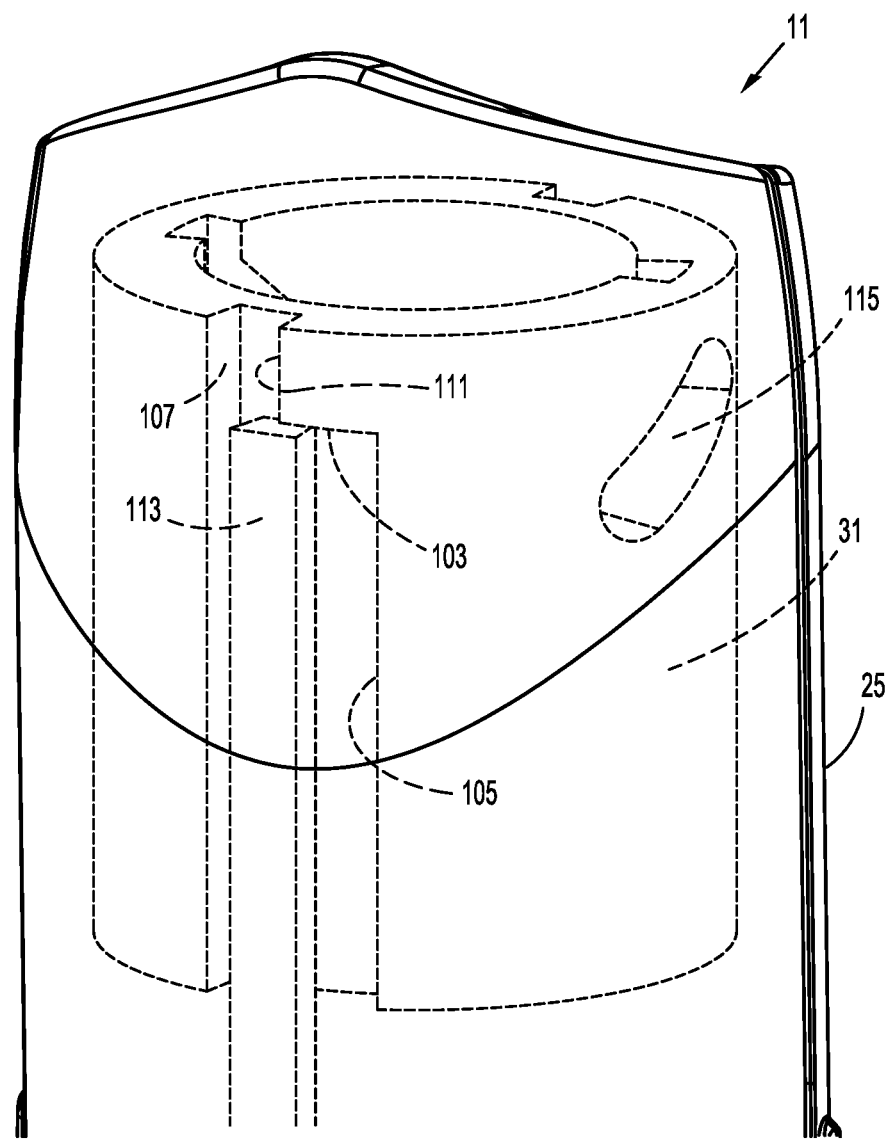
FIG. 5 is an enlarged view, of the indicated area of detail of FIG. 2, with the outer side portions shown in phantom.
Figure 6:
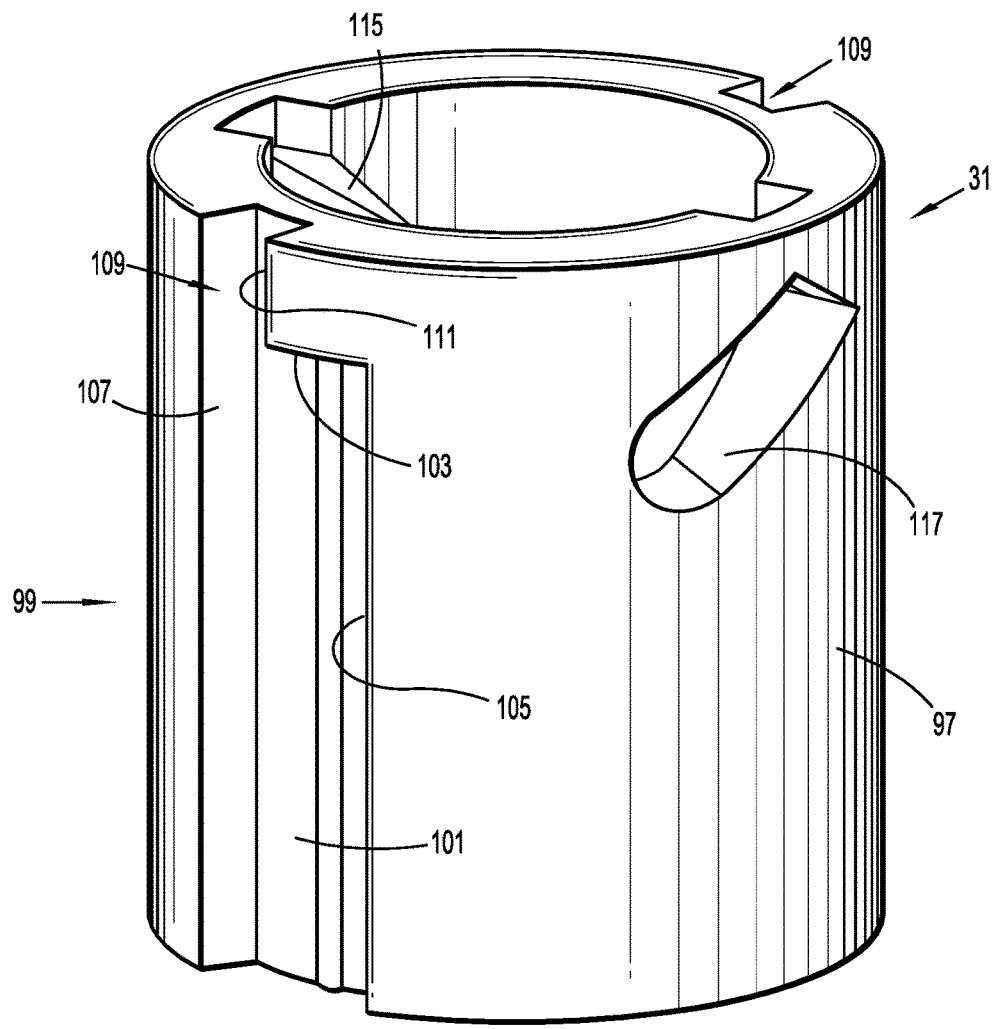
FIG. 6 is a top, perspective view of a collar of the syringe adapter of FIGS. 1-5.
Figure 7:
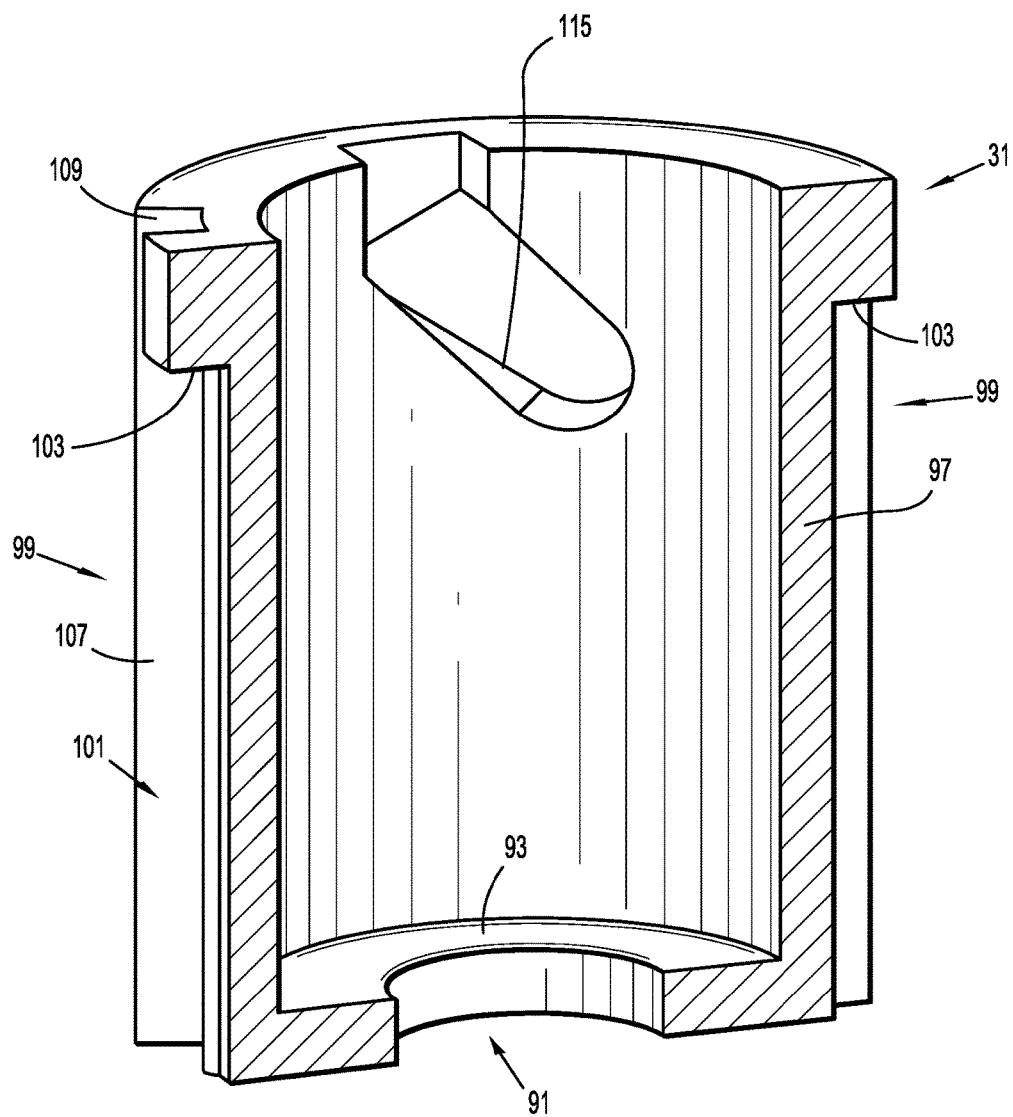
FIG. 7 is a longitudinal cross-sectional view of the collar of FIGS. 5 and 6.

Referring now to FIGS. 3-7, collar 31 is generally cylindrical in shape corresponding to the shape of cavity 41 of housing 25. Collar 31 includes a proximal end wall 93 and a side wall 97 extending from proximal wall 93. Side wall 97 of collar 31 includes two opposed exaggerated angled L-shaped tracks 99 formed in an outer surface thereof, one of which can be seen in FIGS. 6 and 7. The other L-shaped track is not shown but is a mirror image of L-shaped track 99 shown. For simplicity, reference numeral 99 will refer to both L-shaped tracks. As seen in FIG. 6, each track 99 has a lower portion 101 defined by an upper stop wall or shoulder 103 and first and second lateral, longitudinally extending side walls 105, 107. Each track 99 further has a through portion 109 defined by second side wall 107 and a third side wall 111 which is on an end of upper stop wall 103.

On the inside surface of housing 25, facing collar 31 and projecting into each of the two L-shaped tracks 99, are two opposed longitudinally extending male ribs 113, one of which 113 can be seen in FIG. 5. The other rib is not visible but is a mirror image of visible rib 113. For simplicity reference number 113 will refer to both ribs. Each of the two ribs 113 is parallel relative to axis 37. Each rib 113 has a width which is slightly less than the gap between the second side wall 107 and the third side wall 111 defining the through portion 109.

In operation, each rib 113 cooperates with a respective L-shaped track 99 in an identical manner to permit limited rotational and axial movement of collar 31, as described herein. Specifically, contact between each rib 113 and respective first side wall 105 and second side wall 107, with respective upper stop wall 103 riding along rib 113, limits the rotational movement of collar 31 to about 6°, while collar 31 is constrained to move axially along axis 37. In this position, collar 31 supports distal seal 73 of shuttle 29 across opening 39 of housing 25.

After approximately 6° of rotational movement of collar 31, each rib 113 enters respective through portions 109 of L-shaped tracks 99, wherein contact between each rib 113 and respective second side wall and third side wall 107, 111 permits collar 31 to move axially along axis 37, but constrains collar 31 from further rotational movement. With each rib 113 in respective through portions 109, collar 31 can move axially along axis 37 toward proximal end 35 of housing 25 so that tip 61 of needle 27 can pierce abutting seals 23, 73 to place the syringe adapter 11 in an open state. Alternatively, collar 31 can move axially toward distal end 33 of housing 25 so that tip 61 of needle 27 exits seals 23, 73 and re-enters lumen 81 of shuttle 29 to place syringe adapter 11 in the closed state.

Side wall 97 of collar 31 further includes helical tracks 115, 117 formed in an outer surface thereof. Guide pins 53, 55 of any male stem 19 are received in a respective helical track 115 or 117 for purposes of rotating collar 31 and holding seals 23, 73 in abutment with one another, as will now be described.

With reference to FIGS. 32-38, syringe adapter 11 (or syringe adapter 611, see FIGS. 17-24) operates in substantially a two-step manner. Initially, a male stem 19 supporting a seal 23, such as in the vial adapter 13 (not shown), the patient push adapter 15 (as shown in FIGS. 32-38) or the I.V. bag adapter 17 (not shown), is held in abutment with distal seal 73 of shuttle 29. Then, the held-together or abutting seals 23, 73 are pierced with the tip 61 of needle 27 so that needle 27 can enter the lumen 21 of male stem 19 to open the fluid path through syringe adapter 11, thereby placing syringe adapter 11 in the open state and in fluid communication with the vial adapter 13, the patient push adapter 15 or the I.V. bag adapter 17.

Figure 32:
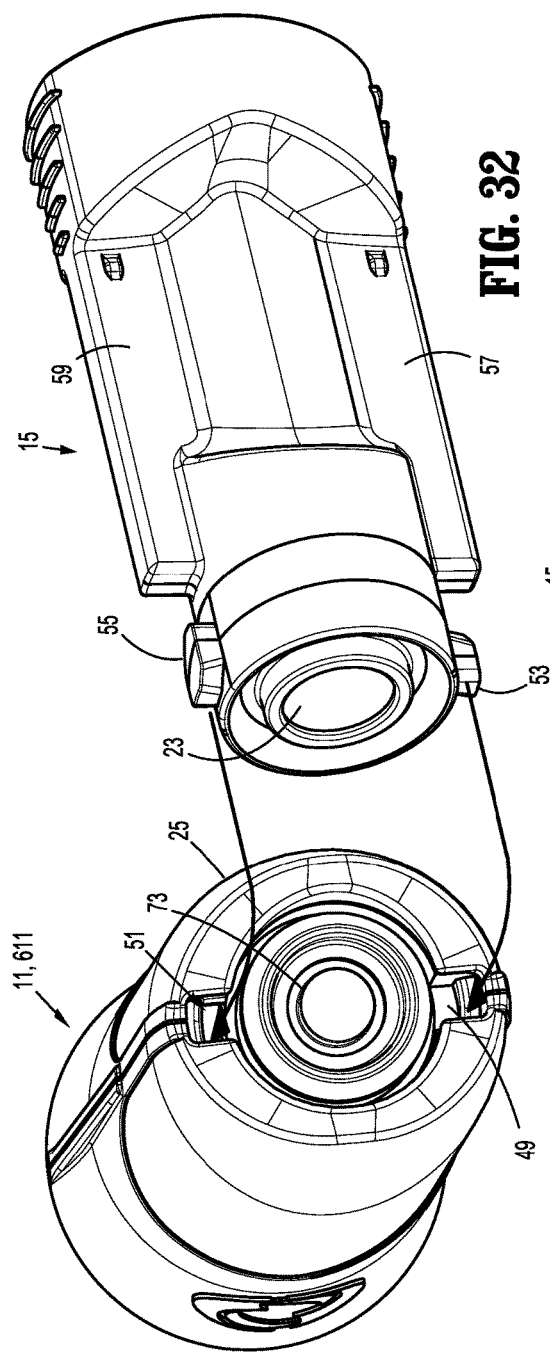
FIGS. 32-38 illustrate a sequence of fluidly connecting a syringe adapter and a patient push adapter.
Figure 33:
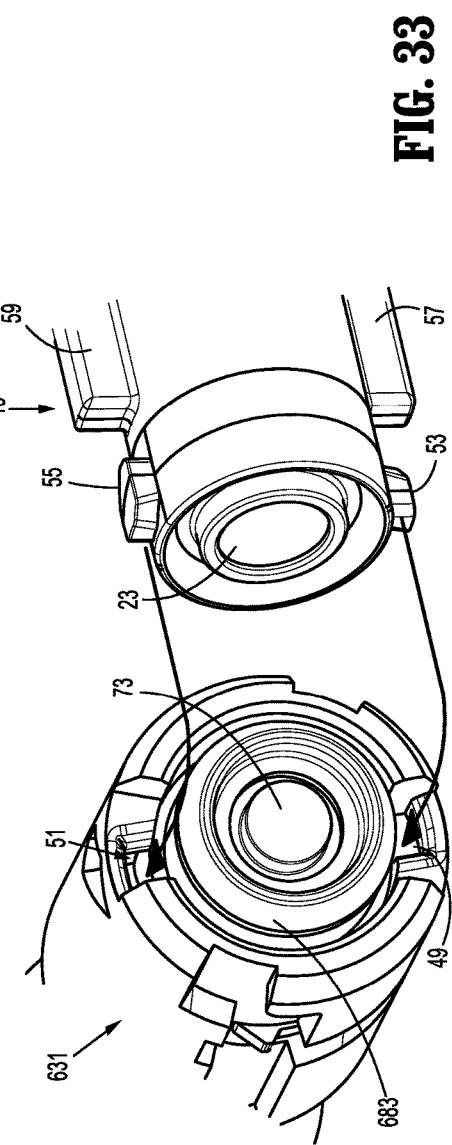
Figure 34:
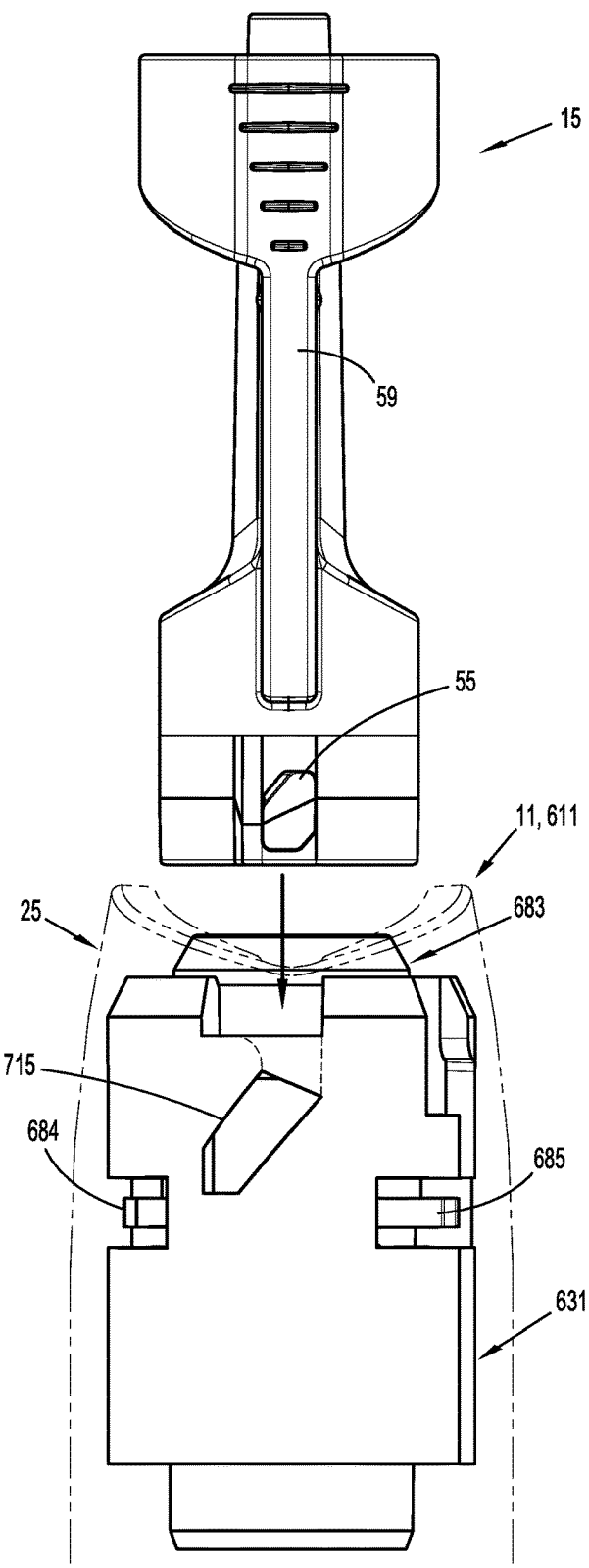
Figure 35:
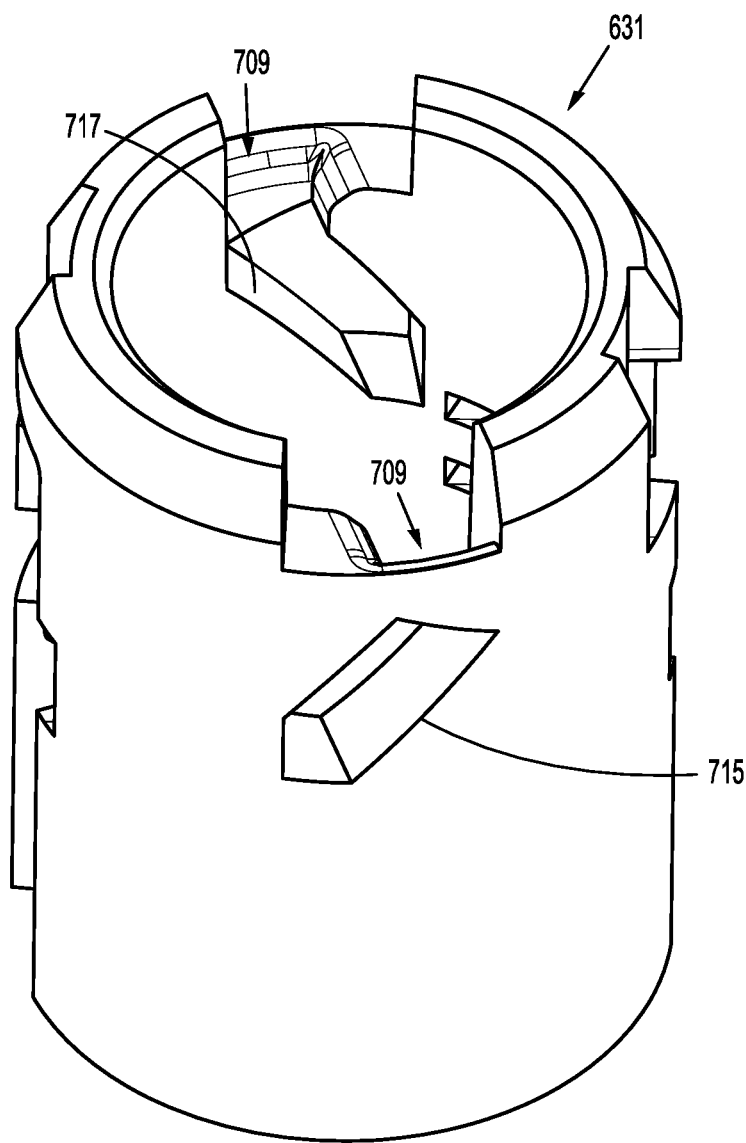
Figure 36:
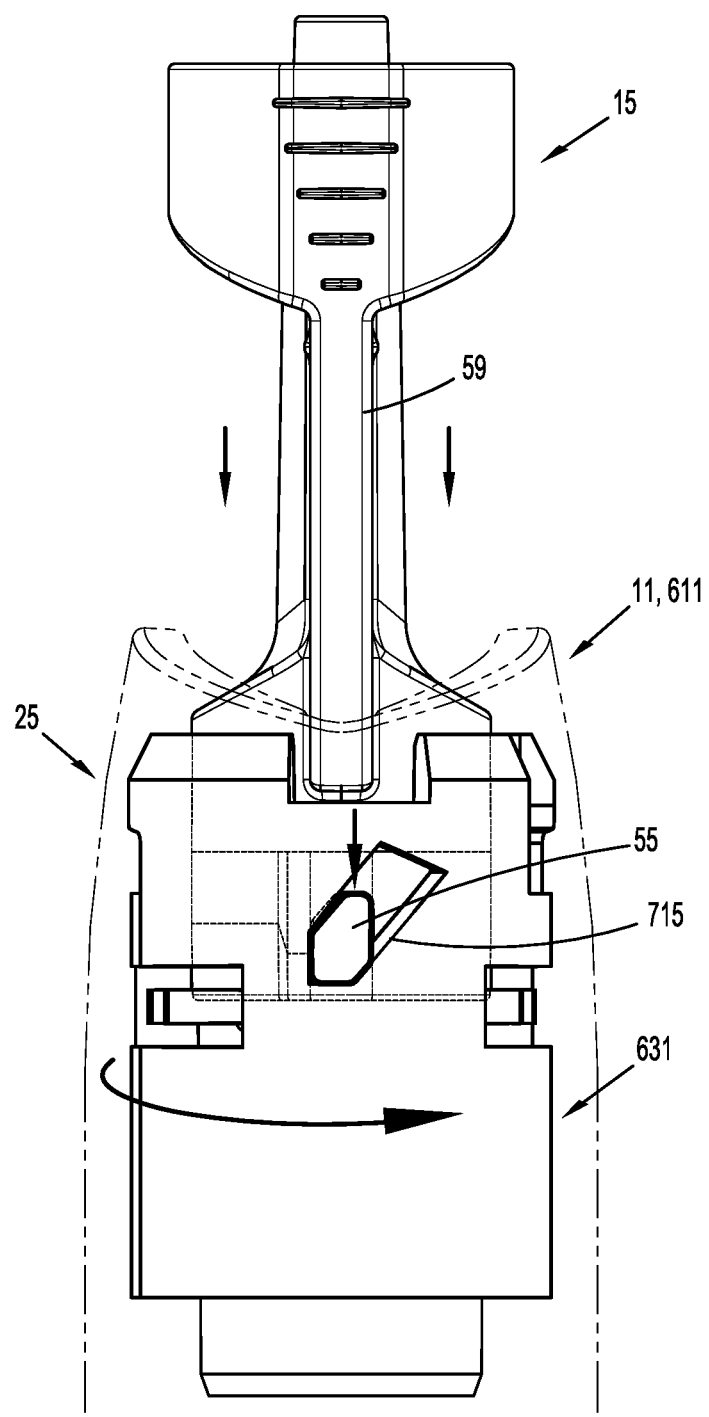
Figure 37:
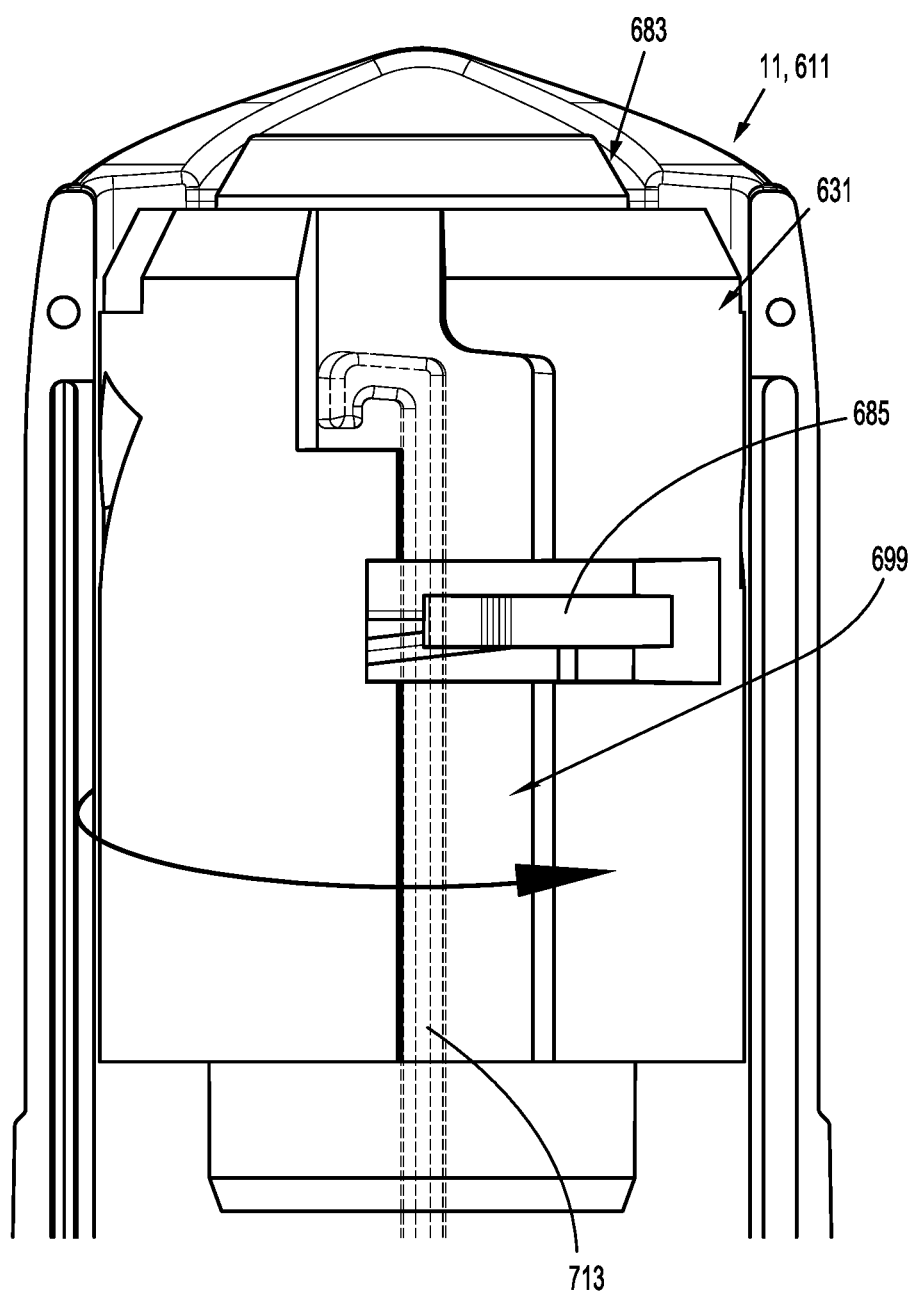

More specifically, in the initial step, as seen in FIGS. 32-34, diametrically opposed, radially extending guide pins 53, 55 of male stem 19 (of, for example, patient push adapter 15) and diametrically opposed, radially extending guide surfaces 57, 59 of male stem 19 are first inserted into respective slots 49, 51 of housing 25 with stem seal 23 of male stem 19 in abutment with distal seal 73 of shuttle 29. Next, stem seal 23 of male stem 19 enters cavity 41 (see FIGS. 4, 38) of housing 25 and guide pins 53, 55 of male stem 19 enter a respective helical track 115, 117 (or 715, 717) of collar 31 (or 631). Simultaneously, shuttle 29 moves axially along axis 37 toward end wall 93 of collar 31 (or 631) and proximal end 35 of housing 25, against spring 95 because collar 31 (or 631) is axially constrained by contact between each rib 113 (or 713) and a respective upper stop or side wall 103 of collar 31 (or 631). Due to the axial constraint imposed on collar 31 (or 631) by each rib 113 (or 713) and respective upper side walls 103, shuttle 29 will move axially toward proximal end 35 of housing 25 until barrel 83 of shuttle 29 bottoms out against end wall 93 of collar 31 (or 631).

Axial movement of guide pins 53, 55 of male stem 19, within a respective collar helical track 115, 117 (or 715, 717), while collar 31 (or 631) is axially constrained, causes collar 31 (or 631) to rotate (counterclockwise as illustrated in the FIGS. 36 and 37) and each of the two upper side walls 103 of collar 31 (or 631) to slide along a respective rib 113 (or 713). As mentioned above, this rotation of collar 31 (or 631) is limited to about 6° by contact between ribs 113 (or 713) and a respective second side wall 107. Male stem 19 is unable to rotate as male stem 19 is inserted into syringe adapter 11 (or 611) because guide surfaces 57, 59 of male stem 19 are constrained within slots 49 and 51 of housing 25.

The restraint on further rotation of collar 31 (or 631), provided by contact between the ribs 113 (or 713) and the respective second side walls 107, in turn, limits further axial movement of male stem 19 because the guide pins 53, 55 of male stem 19 are now axially constrained by the helical tracks 115, 117 (or 715, 717) of collar 31 (or 631). When shuttle 29 is bottomed out against end wall 93 of collar 31 (or 631), further axial movement of shuttle 29 relative to collar 31 (or 631) is prevented. The result is that seal 23 of male stem 19 is held in abutment against distal end seal 73 of shuttle 29. Tip 61 of needle 27 remains axially spaced from abutting seals 23, 73 and there is no fluid flow through syringe adapter 11 (or 611).

Figure 38:
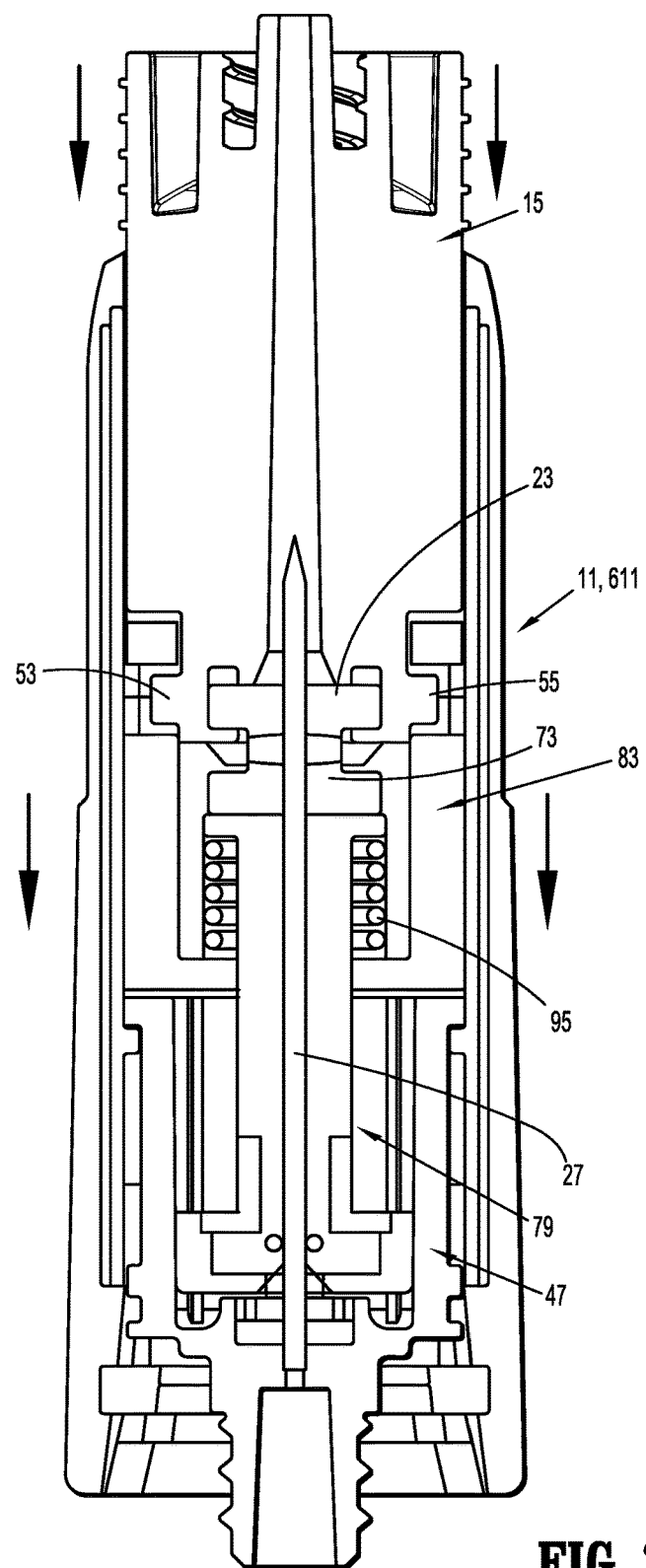

In the following step, as seen in FIG. 38, the user pushes male stem 19 and abutting seals 23, 73 further into cavity 41 of housing 25 (see FIGS. 4, 38) of syringe adapter 11 (or 611). Further axial movement of shuttle 29 and collar 31 is possible now because collar 31 has been rotated so that through portion 109 of each collar L-shaped track 99 (see FIGS. 5-7) is in alignment with a rib 113 (or 713), wherein ribs 113 (or 713) are between second and third side walls 107, 111 (see FIGS. 5-7). Further movement of male stem 19 into cavity 41 (see FIG. 4) moves collar 31 (or 631) and abutting seals 23, 73 toward tip 61 of needle 27 causing tip 61 of needle 27 to pierce the abutting seals 23, 73 and further causing needle 27 to enter lumen 21 of male stem 19 to open the fluid path through syringe adapter 11 (or 611), thereby placing syringe adapter 11 (or 611) in the open state and in fluid communication with the vial adapter 13 (not shown), the patient push adapter 15 or the I.V. bag adapter 17 (not shown). Fluids can now flow from needle 27 toward the vial adapter 13, the patient push adapter 15 or the I.V. bag adapter 17, or can flow in a reverse direction.

To remove the male stem 19 of the vial adapter 13 (not shown), the patient push adapter 15 or the I.V. bag adapter 17 (not shown) from syringe adapter 11 (or 611), the adapter 13, 15, or 17 is pulled fully away from the distal end 33 of housing 25. The process described above takes place in reverse, thereby stopping a flow of fluid once needle tip 61 is fully retracted within lumen 81 of shuttle 29 (see FIG. 4), thereby placing the syringe adapter 11 (or 611) into the closed state.

Figure 11:
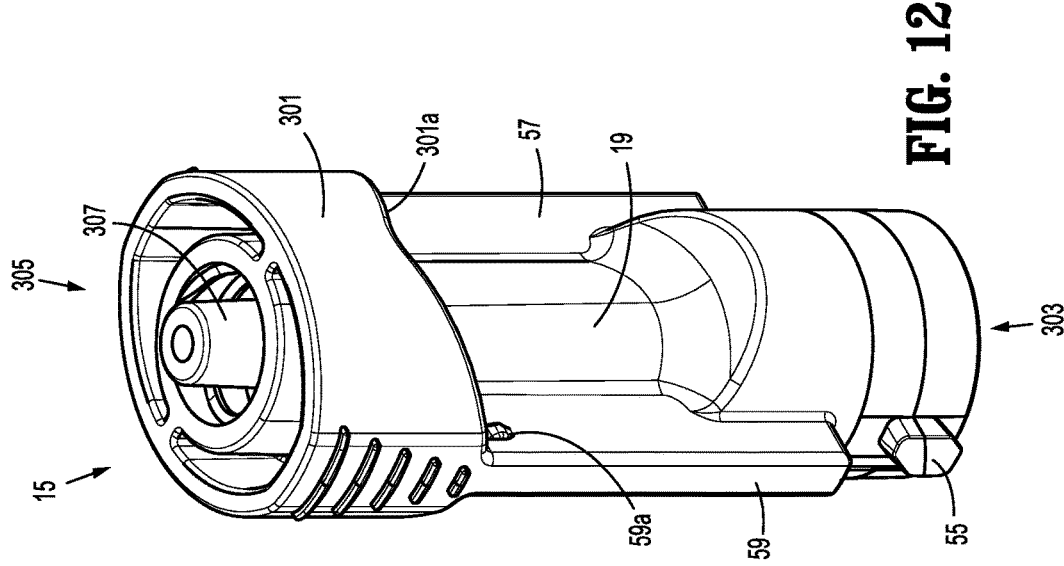
FIG. 11 is a top, perspective view of a patient push adapter of the closed fluid transfer system of FIG. 1.
Figure 12:
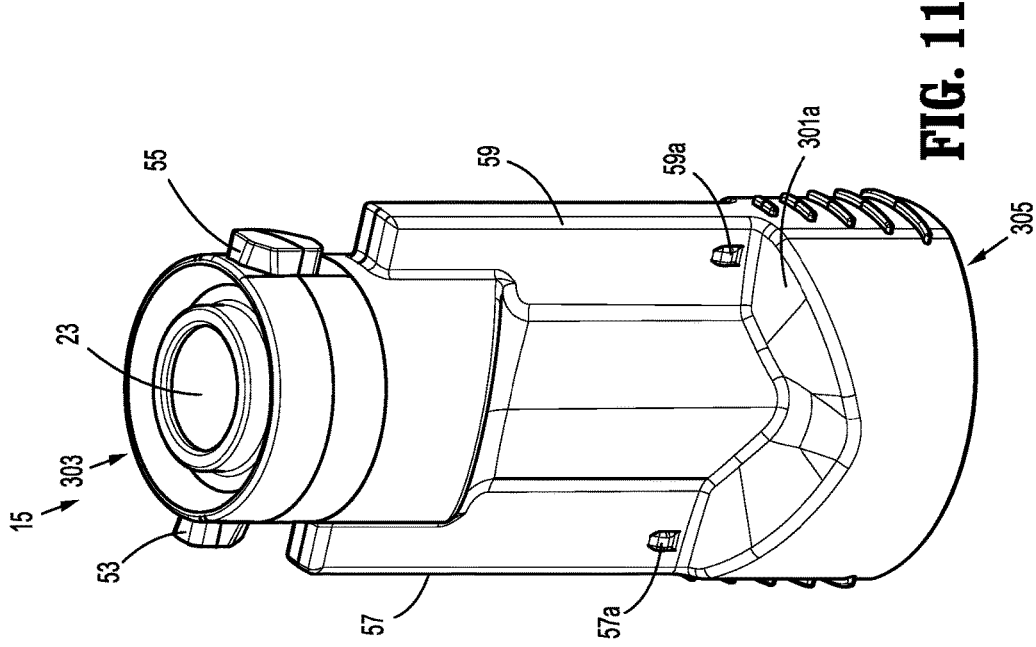
FIG. 12 is a bottom, perspective view of a patient push adapter of the closed fluid transfer system of FIG. 1.
Figure 13:
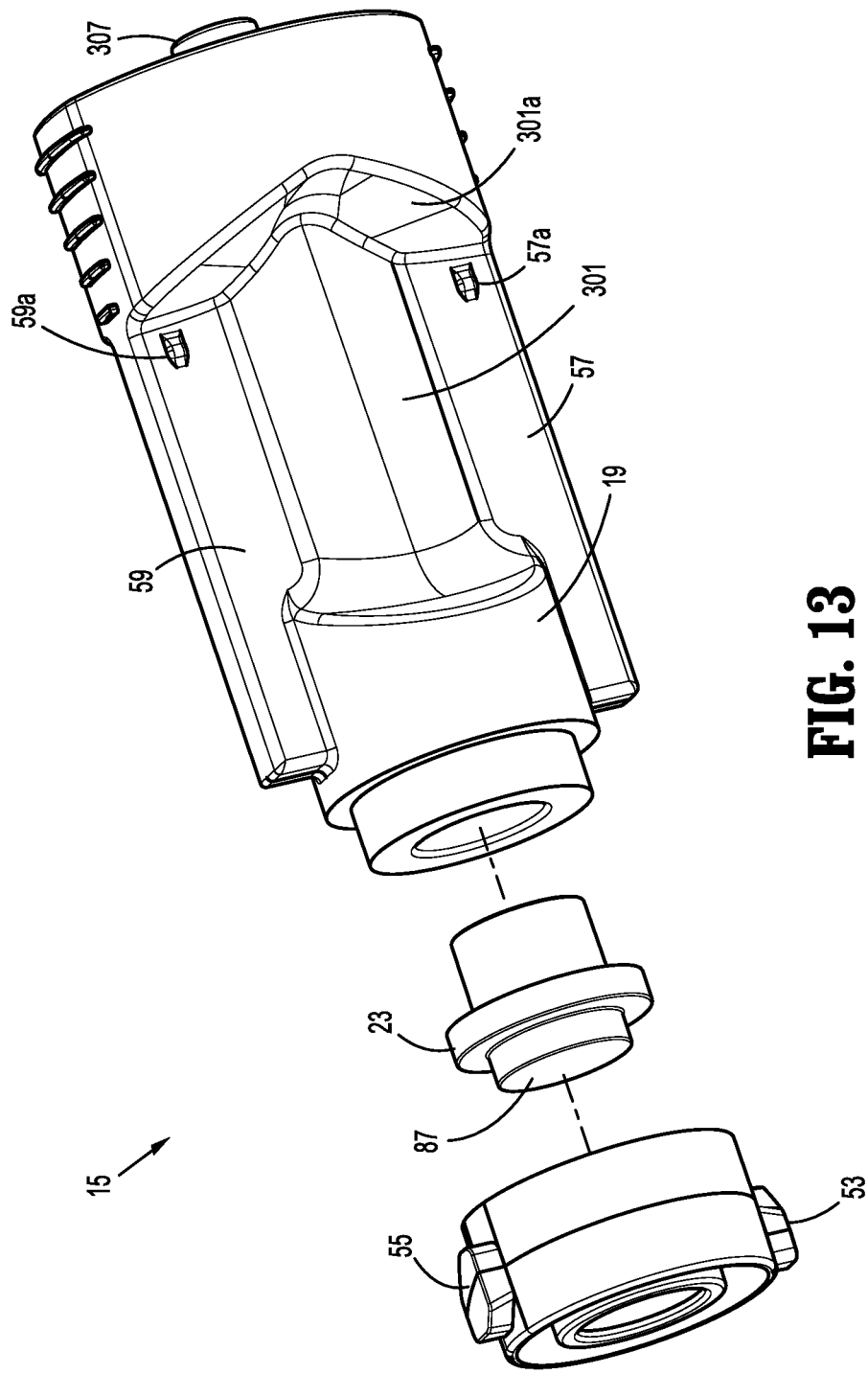
FIG. 13, is a perspective view, with parts separated, of the patient push adapter of FIGS. 11 and 12.
Figure 14:
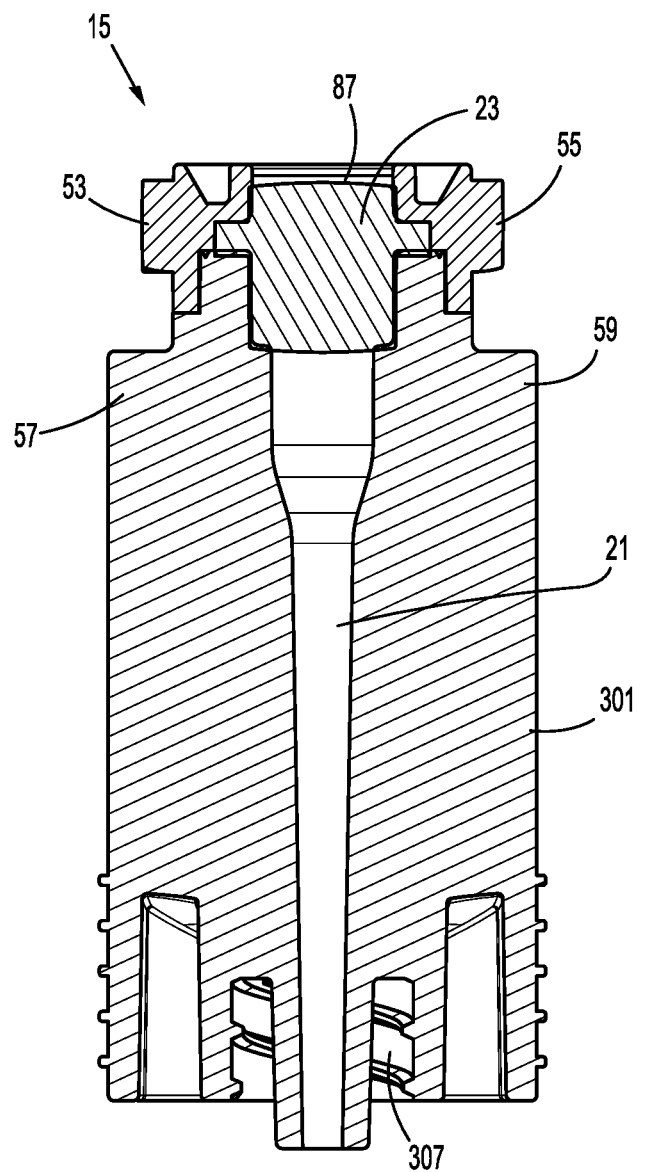
FIG. 14 is a longitudinal, cross-sectional view of the patient push adapter of FIGS. 11-13.

In accordance with the present disclosure, as seen in FIGS. 2-5, it is further contemplated that distal end 33 of housing 25 of syringe adapter 11 may have a substantially sinusoidal distal profile or distal end surface 33a (see FIG. 2), wherein opposed slots 49, 51 of syringe adapter 11 are disposed at a respective opposed nadir or low point of distal end surface 33a. Meanwhile, as seen in FIGS. 11-13, body 301 of patient push adapter 15 may include a substantially sinusoidal profile or surface 301a extending therearound, wherein opposed guide surfaces 55, 57 of patient push adapter 15 are disposed and a respective opposed apex or high point of surface 301a. It is contemplated that distal end surface 33a of syringe adapter 11 and surface 301a of patient push adapter 15 substantially complement one another.

Turning now to FIGS. 1 and 8-10, vial adapter 13 of the closed fluid transfer system 100 of the present disclosure, will be discussed in greater detail. Generally, vial adapter 13 connects to a neck "N" of a vial, bottle, or other container "V" holding liquid "L" to be extracted or into which liquid is to be delivered. For convenience, these containers will be referred to collectively by the term "vial." Vial adapter 13 may be provided in sizes and configurations as necessary to attach to commercially-available vials.

Figure 9:
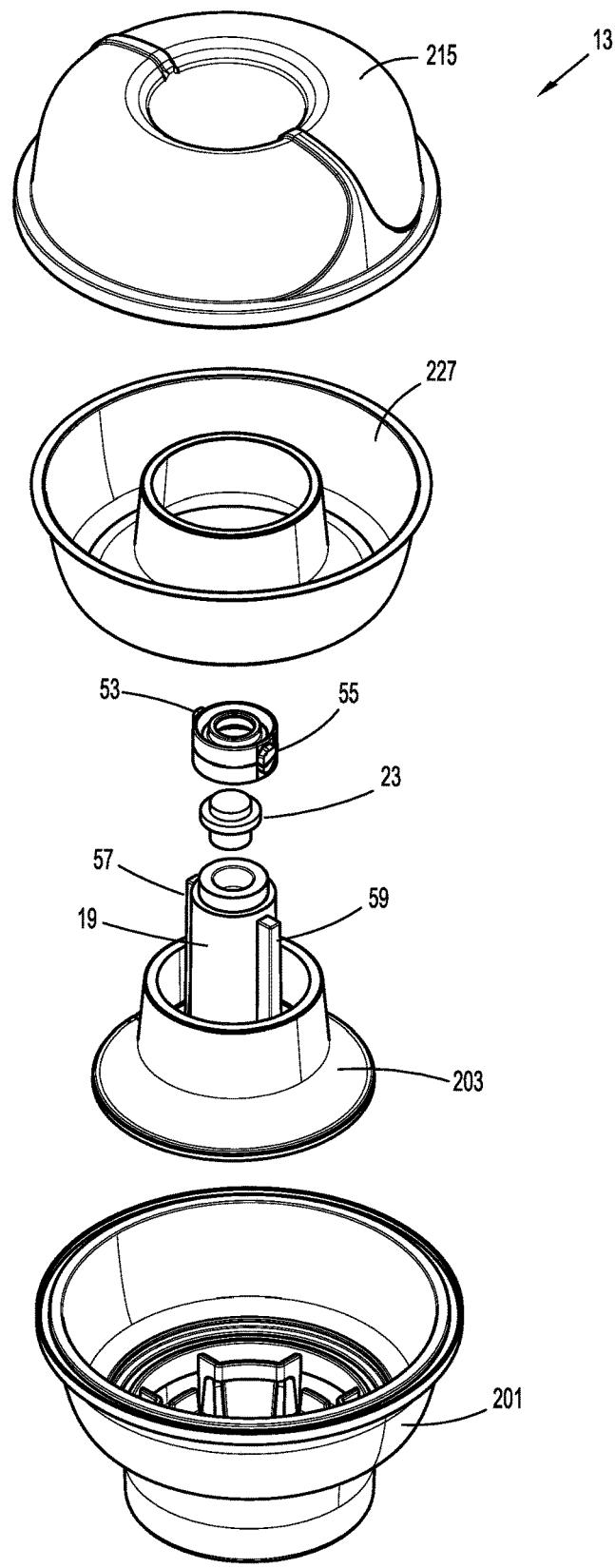
FIG. 9 is a perspective view, with parts separated, of the vial adapter of FIG. 8.
Figure 10:
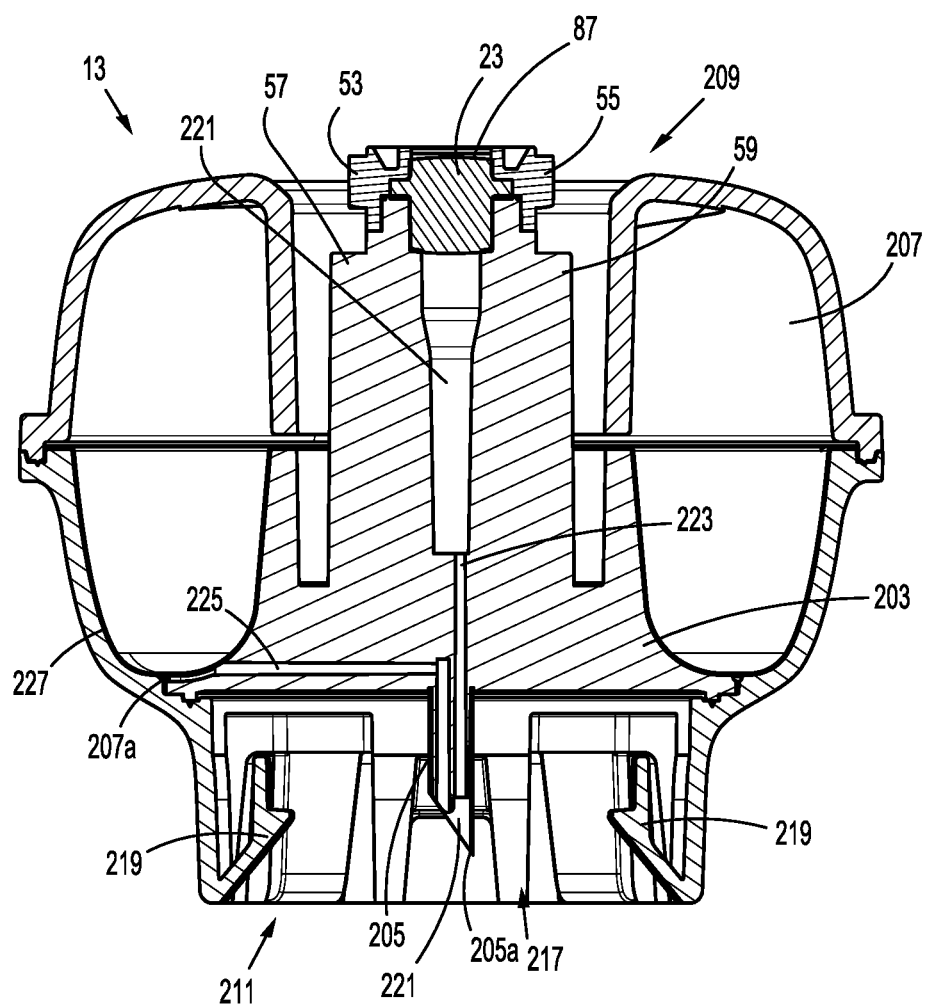
FIG. 10 is a longitudinal, cross-sectional view of the vial adapter of FIGS. 8 and 9.

As illustrated in FIGS. 8-10, vial adapter 13 includes a base 201, an adapter support 203 (including a male stem 19 supporting a seal 23 and including guide pins 53, 55, as described above), a spike 205, and an expansion chamber 207. Vial adapter 13 includes distal and proximal ends 209, 211.

As best shown in FIGS. 9 and 10, base 201 is substantially bowl-shaped and is configured to receive and/or seat an adapter support 203 thereon. Vial adapter 13 includes a toroid-shaped expansion chamber 207, including a bladder 227 and translucent cover 215, seated on an inner rim and an outer rim of base 201. Bladder 227 having a substantially U-shaped radial cross-section including a first annular rim captured between the outer annular rim of base 201 and the outer annular rim of cover 215, and a second annular rim captured between the inner annular rim of base 201 and the inner annular rim of cover 215.

Base 201 of vial adapter 13 includes a circular opening 217 along proximal end 211 thereof into which neck "N" of vial "V" is received. Retainers 219 are provided around the circumference of opening 217 to connect base 201 of vial adapter 13 to form a permanent connection once the neck "N" of the vial "V" is inserted into opening 217.

As seen in FIG. 10, spike 205 extends away from proximal end 211 of base 201 and includes a tip 221 configured to pierce a septum "S" provided on vial "V" when the neck "N" of the vial "V" is inserted into opening 217 of base 201. Spike 205 has a length sufficient to extend into the vial "V". Spike 205 is preferably made of plastic, however, it is envisioned that spike 205 may preferably support a metallic piercing member or hypo-tube 205a to assist in the ability of spike 205 to penetrate the septum "S" of the vial "V".

As seen in FIG. 10, spike 205 and adapter support 203 define two ducts 223, 225. A first duct 223 extends between tip 221 of spike 205 and lumen 21 of male stem 19, and is provided to permit fluid flow between the vial "V" and male stem 19. As described above, opening 63 of tip 61 of needle 27 extends into lumen 21 to extract or deliver liquid through duct 223 when syringe adapter 11 is in the open state. A second duct 225 extends between tip 221 of spike 205 and a first cavity 207a of chamber 207 defined within expansion chamber 207 when toroid-shaped bladder 227 is deflated. Chamber 207a of expansion chamber 207 expands upon a movement of bladder 227 when air or other gas is injected into male stem 19 and duct 223 from a syringe "T" that is attached to syringe adapter 11.

In operation, vial adapter 13 is initially connected to neck "N" of vial "V" with spike 205 piercing septum "S" of vial "V" such that ducts 223, 225 of spike 205 extend into the vial "V". Syringe adapter 11 (as shown and described above) is then attached to male stem 19 of vial adapter 13, as described previously. Liquid "L" may then be extracted from or delivered to the vial "V". If the user wishes to first charge the syringe "T" with air or other gas, then the air may be transferred through the ducts 223, 225 of spike 205 of vial adapter 13 and into first cavity 207a of chamber 207, wherein bladder 227 is moved to accommodate the air. Air in first cavity 207a of chamber 207 moves back into the vial "V" as liquid "L" is withdrawn from the vial "V" and into the syringe "T".

The vial "V" and vial adapter 13 are discarded once the liquid "L" is removed from the vial "V".

It is contemplated and understood that proximal end 211 of base 201 may be sized to accommodate different size necks of different size vials, such as, for example, a 20 mm vial cap of a 60 ml vial; a 28 mm vial cap of a 60 ml vial; and a 13 mm vial cap of a 20 ml vial. Accordingly, a diameter of proximal end of base 201 of vial adapter 13 may be sized appropriately so as to accommodate at least the caps of the vials identified above.

It is contemplated that at least one nub (not shown) may project from a surface of respective guide surfaces 57, 59 of vial adapter 13 and which are configured to snap-fit engage respective complementary detents or recesses defined in slots 49, 51 of syringe adapter 11, or more particularly, an appropriately sized annular rib 49a (see FIG. 3) formed in an inner surface of halves 43, 45 of housing 21 of syringe adapter 11. The interaction of the nubs of the guide surfaces 57, 59 of vial adapter 13 and complementary detents or recesses defined in slots 49, 51 or annular rib 49a (see FIGS. 3 and 4) of syringe adapter 11 provide a user with audible and/or tactile feedback that vial adapter 13 and syringe adapter 11 are properly and fully connected to one another.

Turning now to FIGS. 1 and 11-14, patient push adapter 15 of the closed fluid transfer system 100 of the present disclosure, will be discussed in greater detail. In general, patient push adapter 15 connects to tubing of a patient I.V. set permitting delivery of liquids directly to the patient from a syringe "T" attached to the patient push adapter 15.

The patient push adapter 15 includes a body 301 having respective distal and proximal ends 303, 305. Body 301 of patient push adapter 15 is preferably a one-piece molded plastic part. Distal end 303 of patient push adapter 15 includes a male stem 19 defining a lumen 21, having a seal 23 supported across lumen 21, having guide pins 53, 55 projecting radially outward from on outer surface thereof, and having guide surfaces 57, 59 projecting radially outward from on outer surface thereof. Proximal end 305 of patient push adapter 15 includes a conventional luer connector 307 configured to accept a mating luer connector of a patient I.V. set "IV" (see FIG. 1). Lumen 21 extends through body 301, between seal 23 and luer connector 307, permitting fluid flow between the opening 63 of tip 61 of needle 27 and the luer connector 307, when patient push adapter 15 is properly connected to syringe adapter 11, as described above.

With reference to FIGS. 11-13, it is contemplated that at least one nub 57a, 59a may project from a surface of respective guide surfaces 57, 59 of patient push adapter 15 and which are configured to snap-fit engage respective complementary detents or recesses defined in slots 49, 51 of syringe adapter 11, or more particularly, an appropriately sized annular rib 49a (see FIG. 3) formed in an inner surface of halves 43, 45 of housing 25 of syringe adapter 11. The interaction of nubs 57a, 59a, and complementary detents or recesses defined in slots 49, 51 or annular rib 49a (see FIGS. 3 and 4) of syringe adapter 11 provide a user with audible and/or tactile feedback that patient push adapter 15 and syringe adapter 11 are properly and fully connected to one another.

Guide surfaces 57, 59 of patient push adapter 15 provide a convenient and comfortable surface for a user to grip patient push adapter 15 and to rotate patient push adapter 15 relative to a conventional luer of I.V. set.

Figure 15:
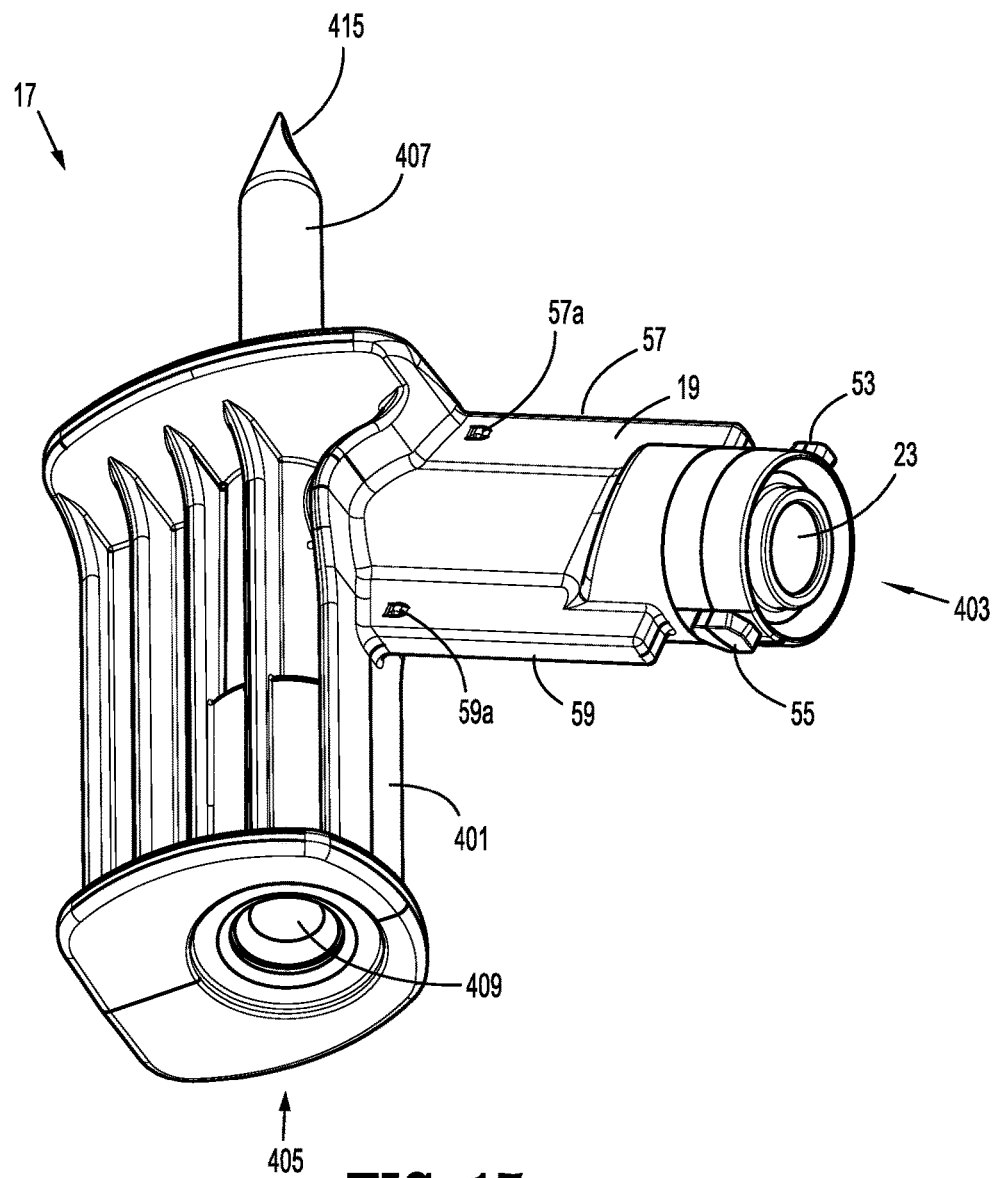
FIG. 15 is a bottom, perspective view of an I.V. bag adapter of the closed fluid transfer system of FIG. 1.
Figure 16:
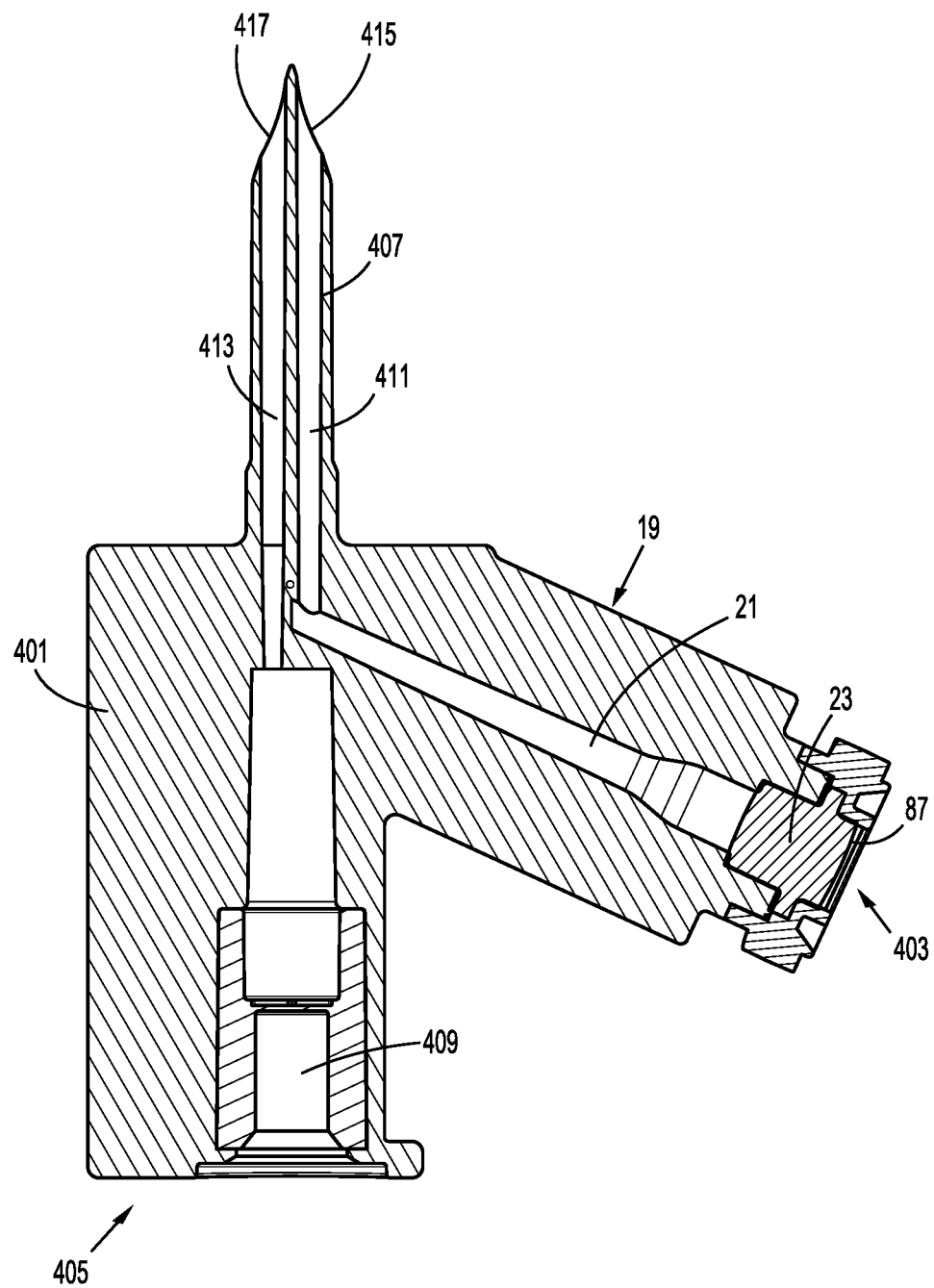
FIG. 16 is a longitudinal, cross-sectional view of the I.V. bag adapter of FIG. 15.

Turning now to FIGS. 1 and 15-16, I.V. bag adapter 17 of the closed fluid transfer system 100 of the present disclosure, will be discussed in greater detail. In general, the I.V. bag adapter 17 enables liquid to be delivered to, or extracted from, a conventional I.V. bag "B" (see FIG. 1). The I.V. bag adapter 17 could also be used as a source of ventilation, permitting air to be delivered from a syringe "I" or other source into the I.V. bag to more rapidly drain the I.V. bag "B" of its liquid contents.

The I.V. bag adapter 17 includes a body 401 having respective distal and proximal ends 403, 405, and a spike 407 extending from body 401. Distal end 403 of I.V. bag adapter 17 includes a male stem 19 defining a lumen 21, having a seal 23 supported across lumen 21, having guide pins 53, 55 projecting radially outward from on outer surface thereof, and having guide surfaces 57, 59 projecting radially outward from on outer surface thereof. Body 401 of I.V. bag adapter 17 is preferably a one-piece molded plastic part. Proximal end 405 of body I.V. bag adapter 17 includes a conventional port 409 which receives a conventional tapered male connector (not shown) of a conventional infusion chamber (not shown) into which liquid drips from the I.V. bag "B". Spike 407 is tapered between distal and proximal ends 403, 405 for insertion into a conventional port (not shown) of I.V. bag "B".

Body 401 of I.V. bag adapter 17 includes two ducts 411, 413. First duct 411 is essentially an extension of lumen 21 through spike 407 extending to an opening 415 in spike 407 which would be within I.V. bag "B" when I.V. bag adapter 17 is attached to the I.V. bag "B". Second duct 413 extends between a second opening 417 in spike 407 and a port 409 for attachment to the infusion chamber (not shown). As described above, opening 63 of tip 61 of needle 27 extends into lumen 21 of male stem 19, when I.V. bag adapter 17 is properly connected to syringe adapter 11, to extract or deliver liquid (or gas) through duct 411 while syringe adapter 11 is in the open state.

In accordance with the present disclosure, a component other than a syringe adapter 11 could be connected to male stem 19 of I.V. bag adapter 17 to deliver gas to I.V. bag "B". Liquid medication delivered through duct 411 may be mixed with the contents of the I.V. bag "B". The liquid in the I.V. bag "B" may then exit the I.V. bag "B" through port 409 and into the infusion chamber for delivery to the patient.

With reference to FIGS. 15 and 16, it is contemplated that at least one nub 57a, 59a may project from a surface of respective guide surfaces 57, 59 of I.V. bag adapter 17 and which are configured to snap-fit engage respective complementary detents or recesses defined in slots 49, 51 of syringe adapter 11, or more particularly, an appropriately sized annular channel 49a (see FIG. 3) formed in an inner surface of halves 43, 45 of housing 25 of syringe adapter 11. The interaction of nubs 57a, 59a and complementary detents or recesses defined in slots 49, 51 or annular rib 49a (see FIGS. 3 and 4) of syringe adapter 11 provide a user with audible and/or tactile feedback that I.V. bag adapter 17 and syringe adapter 11 are properly and fully connected to one another.

Turning now to FIGS. 17-24, a syringe adapter, according to another embodiment of the present disclosure, is generally designated as 611. Syringe adapter 611 is substantially similar to syringe adapter 11 and thus will only be discussed in detail hereinbelow to the extent necessary to describe differences in construction and operation therebetween.

Figure 18:
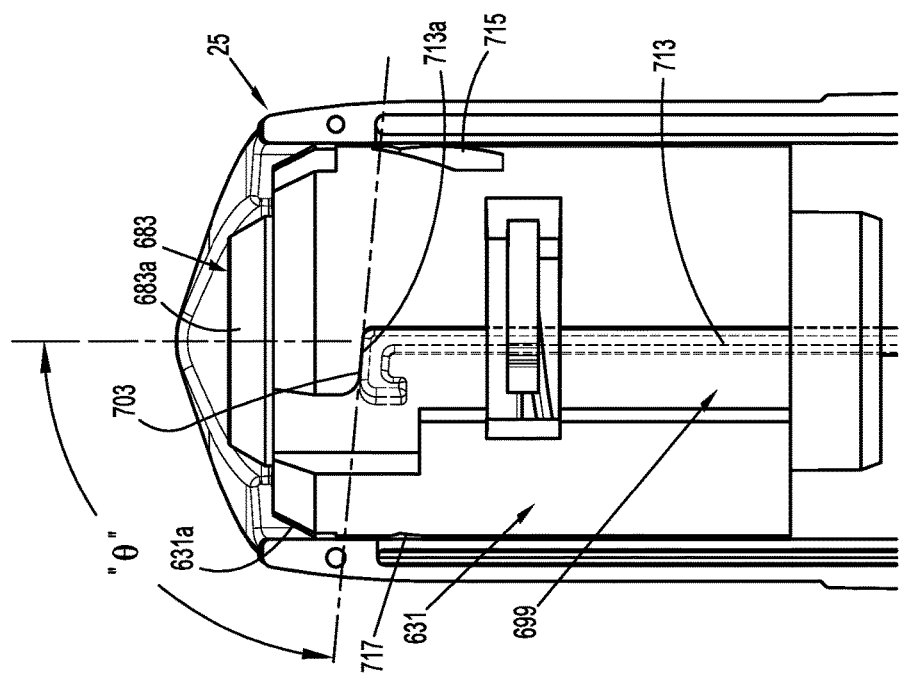
FIG. 18 is a side, elevational view of a distal end of the syringe adapter of FIG. 17, with one housing half removed.
Figure 17:
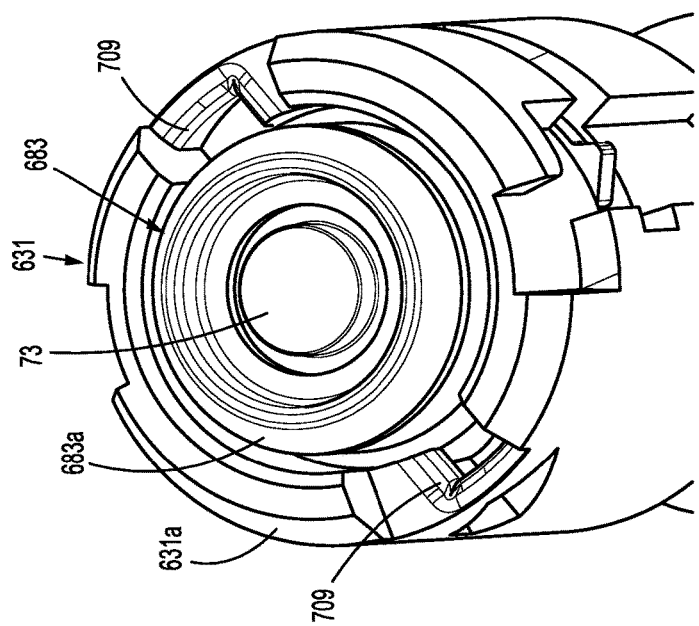
FIG. 17 is a distal, perspective view of a syringe adapter, with the housing removed, according to another embodiment of the present disclosure.

As seen in FIGS. 17-19, a respective distal or leading edge 631a, 683a of collar 631 and barrel 683 is chambered to thereby improve the mating of syringe adapter 611 with vial adapter 13, patient push adapter 15, and I.V. bag adapter 17. Additionally, a lead in for each through portion 709, defined in an outer surface of collar 631, has been chamfered so as to better guide the guide pins 53, 55 of any male stem 19 into through portions 709.

As seen in FIG. 18, upper stop wall 703 of each track 699 of collar 631 is oriented at an angle relative to a longitudinal axis of track 699. In particular, upper stop wall 703 is oriented at an angle "0" of approximately 85° relative to the longitudinal axis of track 699. It is also contemplated that a distal-most surface 713a of ribs 713 is also oriented at an angle that substantially compliments the angle of upper stop wall 703. Such an angle of incline for upper stop wall 703 of each track 699 of collar 631 and of distal-most surface 713a of each rib 713, facilitates the ability of collar 631 to rotate relative to housing 25 of syringe adapter 611.

As illustrated in FIG. 19, collar 631 includes helical tracks 715, 717 formed in an outer surface thereof. Each track 715, 717 defines a pitch or angle relative to a longitudinal axis of collar 631 equal to approximately 50°. In this manner, the angle or pitch of helical tracks 715, 717 of collar 631 is greater than the angle or pitch of helical tracks 115, 117 of collar 31.

Referring now to FIGS. 21-24, syringe adapter 611 includes a lock-out feature that prevents an inadvertent rotation of collar 631, relative to housing 25, prior to engagement of seal 73 by the seal 23 of any of the male stems 19. The lock-out feature includes a shuttle 629 having a relatively larger diameter proximal portion 683a of barrel 683 transitioning to a relatively smaller diameter distal portion 683b of barrel 683. The lock-out feature includes a pair of diametrically opposed resilient lock arms 684, 685 formed in collar 631. Each lock arm 684, 685 extends in a radial direction about collar 631 and includes a first end 684a, 685a integrally formed or extending from collar 631, and a free second end 684b, 685b. The free second end 684b, 685b of each lock arm defines a tooth for engaging a respective rib 713.

Figure 21:
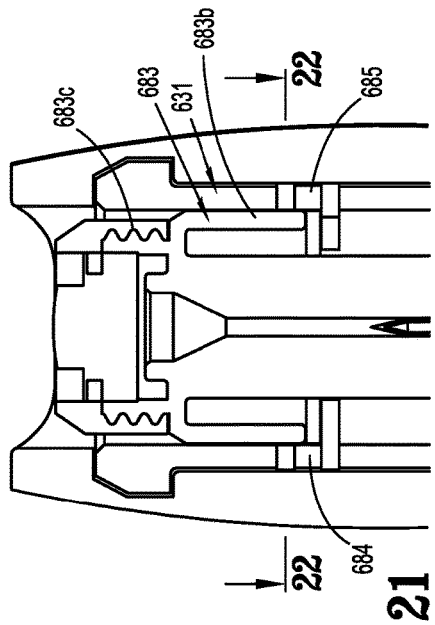
FIG. 21 is a further, longitudinal, cross-sectional view of a distal end of the syringe adapter of FIGS. 17-19, illustrating a locking system of the syringe adapter in a first condition.
Figure 22:
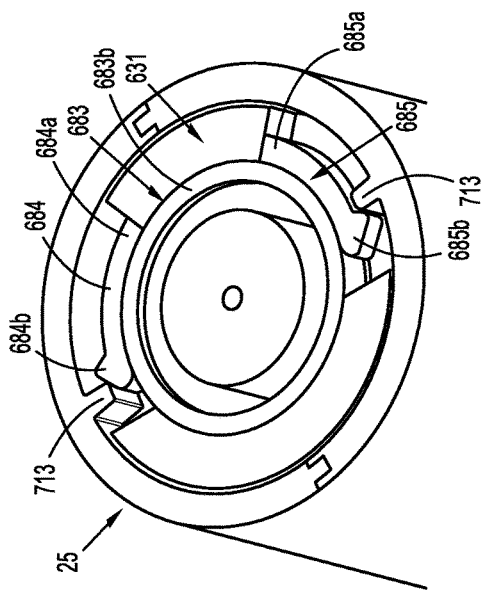
FIG. 22 is a cross-sectional view of the syringe adapter of FIG. 21, as taken through 22-22 of FIG. 21.

In use, when shuttle 629 is in a non-depressed condition, as seen in FIGS. 21 and 22, proximal portion 683a of barrel 683 of shuttle 629 is dimensioned so as to press against resilient lock arms 684, 685 formed in collar 631 or act as a barrier or wall against resilient lock arms 684, 685 formed in collar 631, so as to prevent resilient lock arms 684, 685 from deflecting radially inward and disengaging respective ribs 713. Since the tooth of lock arms 684, 685 is in engagement with respective ribs 713 of housing 25, collar 631 is prevented from rotating relative to housing 25 and thus prematurely enabling collar 631 from being depressed (after rotation) relative to housing 25.

Figure 23:
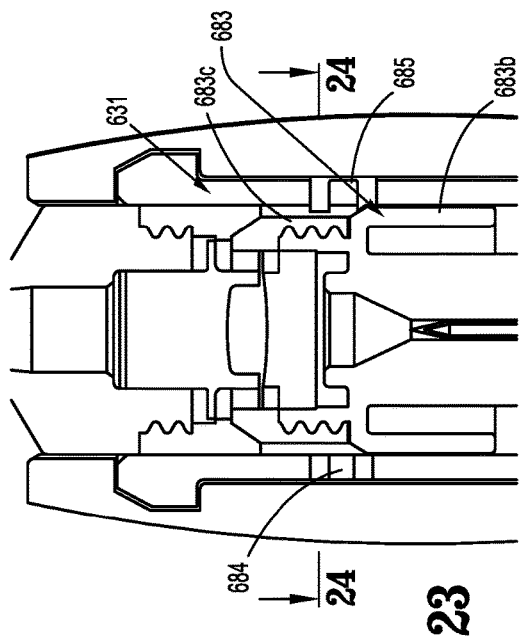
FIG. 23 is a further, longitudinal, cross-sectional view of a distal end of the syringe adapter of FIGS. 17-19, illustrating a locking system of the syringe adapter in a second condition.
Figure 24:
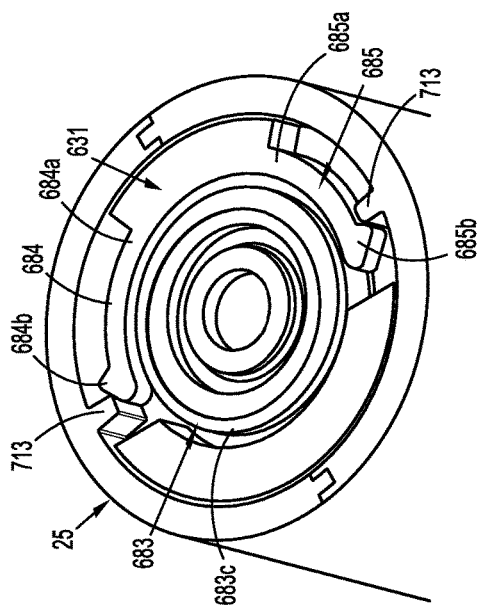
FIG. 24 is a cross-sectional view of the syringe adapter of FIG. 23, as taken through 24-24 of FIG. 22.

As illustrated in FIGS. 23-24, in use, as shuttle 629 is pressed into collar 631, upon a coupling with any of the male stems 19, as described above, distal portion 683b of barrel 683 of shuttle 629 aligns with or comes into registration with lock arms 684, 685 of collar 631. With the resilient lock arms 684, 685 overlying distal portion 683b of barrel 683 of shuttle 629, distal portion 683b of barrel 683 of shuttle 629 is spaced a distance radially inward of lock arms 684, 685 by an amount sufficient to allow lock arms 684, 685 to deflect radially inward and snap over respective ribs 713 as collar 631 is rotated relative to housing 25.

As seen in FIGS. 22 and 24, lock arms 684, 685 are mirrored about a plane extending parallel to a longitudinal axis of collar 631 and extending substantially equally between lock arms 684, 685.

Referring now to FIGS. 25-31, closed fluid transfer system 100, of the present disclosure, may include a universal vial adapter 813. Generally, universal vial adapter 813 connects to various sized caps or necks of vials holding a liquid to be extracted or into which liquid is to be delivered. For example, universal vial adapter 813 may be configured to connect to vials having either a 20 mm vial cap or a 28 mm vial cap. While 20 mm and 28 mm vial caps are identified, it is contemplated that universal vial adapter 813 may be configured and dimensioned to accommodate and/or connect to any size cap of any vial or the like.

Figure 25:
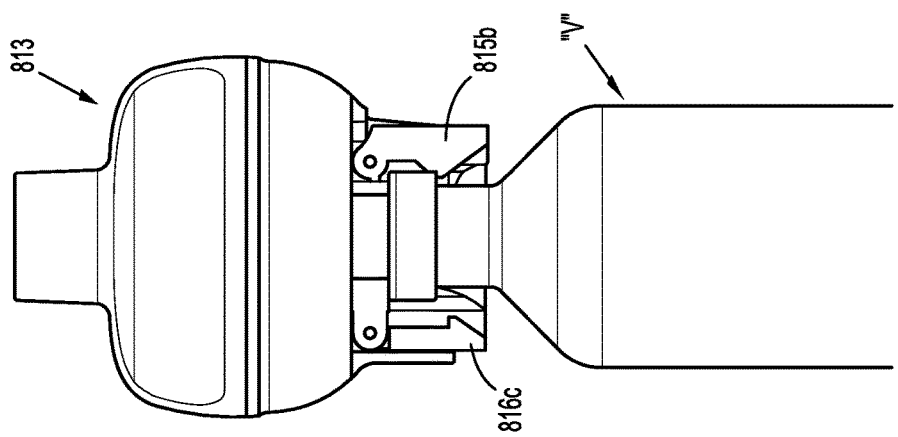
FIG. 25 is a schematic, elevational view of a universal vial adapter according to an embodiment of the present disclosure, shown connected to a vial neck having a first diameter.
Figure 26:
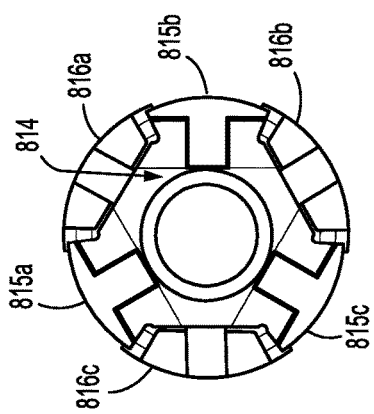
FIG. 26 is a top, plan view of a hub of the universal vial adapter as connected to the vial of FIG. 25.
Figure 27:
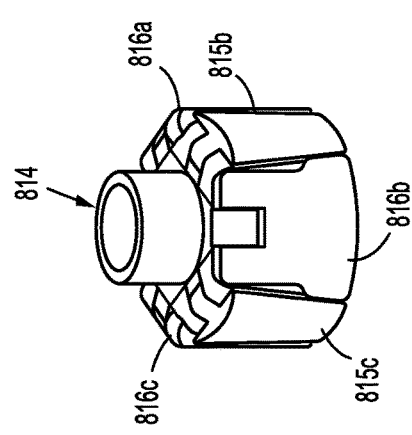
FIG. 27 is a perspective view of the hub of the universal vial adapter as connected to the vial of FIG. 25.
Figure 31:
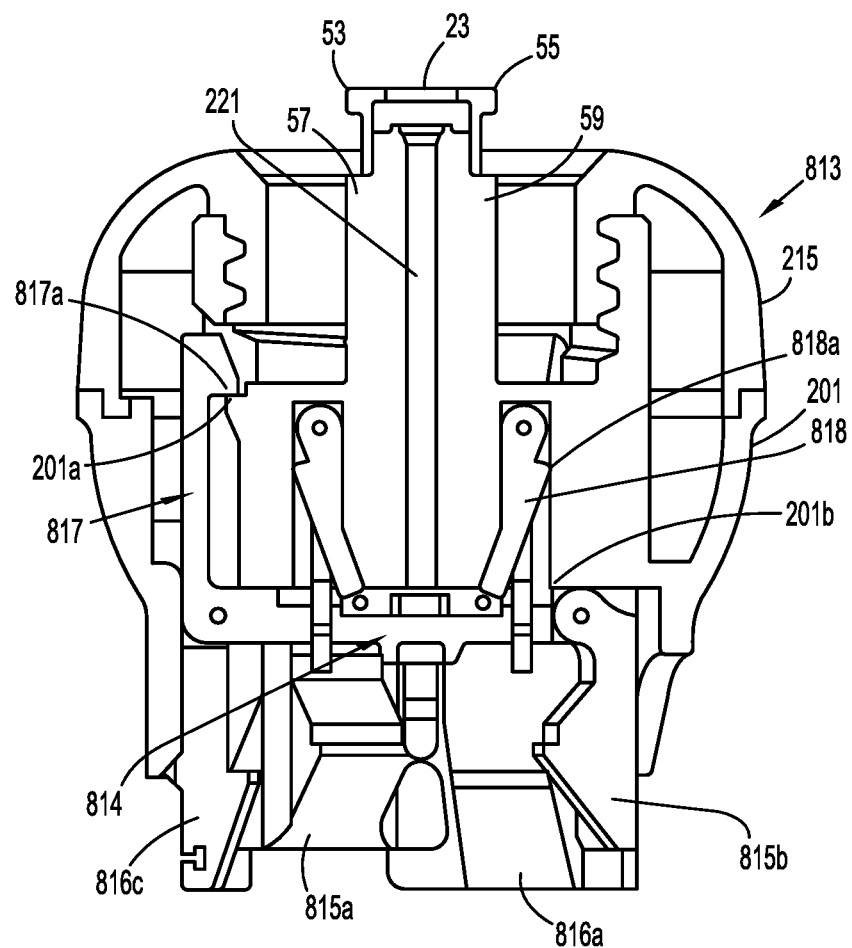
FIG. 31 is a schematic, longitudinal, cross-sectional view of the universal vial adapter of FIGS. 25-30.

Universal vial adapter 813 includes three, equally radially spaced apart first claws 815a, 815b, 815c supported on a hub 814 and which are configured to engage an outer rim of a relatively smaller diametered cap (e.g., a 20 mm vial cap as seen in FIG. 25). Universal vial adapter 813 also includes three, equally radially spaced apart second claws 816a, 816b, 816c supported on a hub 814 and which are configured to engage an outer rim of a relatively larger diametered cap (e.g., a 28 mm vial cap as seen in FIG. 28). Each second claw 816a, 816b, 816c is interposed between adjacent first claws 815a, 815b, 815c.

It is contemplated that each claw 815a, 815b, 815c and each claw 816a, 816b, 816c is biased to a closed condition.

It is further contemplated that hub 814 is slidably disposed within base 201 of universal vial adapter 813. Universal vial adapter 813 includes a locking system including at least one first latch arm 817 having a shoulder 817a which engages a first shoulder 201a of base 201 when hub 814 is in a fully pressed-in condition. The locking system of universal vial adapter 813 includes at least one second latch arm 818 having a shoulder 818a which engages a second shoulder 201b of base 201 when hub 814 is in a fully non-pressed-in condition.

In use, the at least one second latch arm 818 of the locking system maintains hub 814 in the fully non-pressed-in condition until a relatively smaller cap is fully engaged by first claws 815a, 815b, 815c or until relatively larger cap is fully engaged by second claws 816a, 816b, 816c. Once the cap is fully engaged by first claws 815a, 815b, 815c or second claws 816a, 816b, 816c, the at least one second latch arm 818 of the locking system disengages from second shoulder 201b of base 201, allowing hub 814 to be moved to the pressed-in condition. When hub 814 is moved to the pressed-in condition, the shoulder 817a of the at least one first latch arm 817 engages the first shoulder 201a of base 201 to maintain hub 814 in the pressed-in condition.

An important aspect of the present disclosure is the alignment and contact of seal 73 of syringe adapters 11 or 611 with seal 23 of male stems 19 of patient push adapter 13, vial adapters 15 and 815, and I.V. bag adapter 17. Ensuring that seals 73 and 23 are in proper alignment with one another is important to ensure that needle 27 penetrates through both seals 73 and 23 upon complete coupling/connecting of syringe adapters 11, 611 with patient push adapter 13, vial adapters 15 and 815, and I.V. bag adapter 17.

Another important aspect of the present disclosure is the ability of the user to swab, wipe, clean and/or disinfect seals 73 and 23 prior to or following their use.

Also in accordance with the present disclosure, each seal 23 and 73 is provided with a constant pressure radially inward along an entire length of seal 23, 73 such that the distal and proximal surfaces of seals 23, 73 are convex or arc outward. As such, the seal to seal contact between abutting seals 23 and 73 is improved.

While the above disclosure and related figures illustrate syringes, vials, I.V. sets, and I.V. bags as exemplary embodiments, it is envisioned and within the scope of the present disclosure that any of the adapters described herein may be used in cooperation with any fluid container, such as, for example, bottles, test tubes, trays, tubs, vats, jars, bathes, pools, pressure vessels, balloons, ampoules, etc.

It will be understood that various modifications may be made to the embodiments disclosed herein. Therefore, the above description should not be construed as limiting, but merely as exemplifications of preferred embodiments. Those skilled in the art will envision other modifications within the scope and spirit of the claims appended thereto.

What is claimed is:

1. A syringe adapter for a closed fluid transfer system, the syringe adapter including:
    a housing defining an open distal end and an open proximal end;
    a base supported in the open proximal end of the housing and including a syringe adapter luer connector;
    a collar slidably and rotatably supported in the housing, the collar defining a longitudinal opening therethrough;
    a shuttle slidably extending through longitudinal opening of the collar, the shuttle defining a shuttle lumen extending longitudinally therethrough;
    a barrel supported on and extending over a distal end of the shuttle, the barrel defining a central opening aligned with the shuttle lumen;
    a biasing member interposed between the collar and the shuttle for urging the collar away from the shuttle; and
    a seal interposed between the shuttle and the barrel, wherein the seal extends across the shuttle lumen and the central opening of the barrel.

2. The syringe adapter according to claim 1, further comprising a needle defining a lumen therethrough, the needle having a proximal end supported in the base such that the lumen of the needle is in fluid communication with the luer connector.

3. The syringe adapter according to claim 2, wherein the needle has a sharpened distal tip disposed within the shuttle lumen when the shuttle is in a distal-most position.

4. The syringe adapter according to claim 3, wherein the housing defines a pair of opposed longitudinally extending slots opening from the open distal end of the housing, and wherein the housing includes a pair of opposed longitudinally extending ribs projecting from an inner surface thereof.

5. The syringe adapter according to claim 4, wherein the collar defines a pair of opposed L-shaped tracks formed in an outer surface thereof and configured to receive a respective longitudinally extending rib of the housing therein, and wherein the collar defines a pair of opposed helical tracks opening from a distal surface of the collar, the opposed helical tracks are aligned with a respective slot of the housing when the collar is in a distal-most position.

6. The syringe adapter according to claim 5, wherein the syringe adapter is movable from a closed state to an open state;
    wherein in the closed state the tip of the needle is disposed within the shuttle lumen, the shuttle is disposed at the distal-most position, and the collar is disposed at a distal-most position; and
    wherein the syringe adapter is movable from the closed state to the open state by:
        inserting a pair of opposed radially extending guide pins of a male stem of a second adapter into the respective slots of the housing of the syringe adapter, whereby a second adapter seal of the second adapter abuts a first adapter seal of a first adapter;
        advancing the second adapter male stem into the open distal end of the housing such that the guide pins of the second adapter enter into the respective helical track of the collar to (1) rotate the collar relative to the housing of the syringe adapter and (2) align the ribs of the housing with a through portion of the collar; and further advancing the second adapter male stem into the open distal end of the housing causing the collar to move proximally which causes the shuttle to move proximally until the tip of the needle penetrates through the abutting seals, whereby the syringe adapter is in the open state and fluidly interconnects a syringe with the second adapter.

7. The syringe adapter according to claim 1, wherein the syringe adapter includes a lock out system having:

a lock collar including at least one lock arm extending in a radial direction about the lock collar, wherein each lock arm includes a first end integral with the lock collar and a second free end defining a tooth extending radially outward and being dimensioned to contact a longitudinally extending rib of the housing; and a shuttle including a relatively larger diameter proximal portion and a relatively smaller diameter distal portion;

wherein, when the shuttle is in the distal-most position, each lock arm is in registration with the relatively larger diameter portion of the shuttle thereby inhibiting each lock arm from deflecting radially inward; and wherein, when the shuttle is moved proximally, the relatively smaller diameter portion of the shuttle is moved into registration with each lock arm thereby permitting each lock arm to deflect radially inward and to permit the lock collar to rotate.

8. The syringe adapter according to claim 1, wherein the seal is made from polyisoprene.

* * * * *